(12) United States Patent
Abel et al.

(10) Patent No.: US 7,160,867 B2
(45) Date of Patent: Jan. 9, 2007

(54) RAPAMYCIN CARBOHYDRATE DERIVATIVES

(75) Inventors: Mark Abel, Edmonton (CA); Roman Szweda, Edmonton (CA); Daniel Trepanier, Edmonton (CA); Randall W Yatscoff, Edmonton (CA); Robert T. Foster, Edmonton (CA)

(73) Assignee: Isotechnika, Inc., Edmonton (CA)

( * ) Notice: Subject to any disclaimer, the term of this patent is extended or adjusted under 35 U.S.C. 154(b) by 322 days.

(21) Appl. No.: 10/845,747

(22) Filed: May 13, 2004

(65) Prior Publication Data

US 2004/0235762 A1 Nov. 25, 2004

Related U.S. Application Data

(60) Provisional application No. 60/562,840, filed on Apr. 16, 2004, provisional application No. 60/546,240, filed on Feb. 20, 2004, provisional application No. 60/471,367, filed on May 16, 2003.

(51) Int. Cl.
*A61K 31/70* (2006.01)
*A61K 31/44* (2006.01)
*C07H 15/00* (2006.01)
*C07D 487/00* (2006.01)
*A61F 13/00* (2006.01)

(52) U.S. Cl. ............... 514/28; 536/6.5; 536/7.1; 536/18.1; 540/456; 514/291; 424/422; 623/1.11; 623/1.23

(58) Field of Classification Search ............ 514/28, 514/29, 291; 536/6.5, 7.1, 18.1; 424/422; 623/1.11, 1.23; 540/456
See application file for complete search history.

(56) References Cited

U.S. PATENT DOCUMENTS

| | | |
|---|---|---|
| 3,929,992 A | 12/1975 | Sehgal et al. |
| 4,316,885 A | 2/1982 | Rakhit |
| 4,650,803 A | 3/1987 | Stella et al. |
| 5,023,262 A | 6/1991 | Caufield et al. |
| 5,023,263 A | 6/1991 | Von Burg |
| 5,100,899 A | 3/1992 | Calne |
| 5,162,333 A | 11/1992 | Failli et al. |
| 5,212,155 A | 5/1993 | Calne |
| 5,258,389 A | 11/1993 | Goulet et al. |
| 5,260,300 A | 11/1993 | Hu |
| 5,262,423 A | 11/1993 | Kao |
| 5,308,847 A | 5/1994 | Calne |
| 5,358,944 A | 10/1994 | Caufield |
| 5,362,718 A | 11/1994 | Skotnicki et al. |
| 5,378,696 A | 1/1995 | Caufield |
| 5,403,833 A | 4/1995 | Calne |
| 5,432,183 A | 7/1995 | Schulte |
| 5,457,111 A | 10/1995 | Luly et al. |
| 5,461,058 A | 10/1995 | Calne |
| 5,506,233 A | 4/1996 | Hauske et al. |
| 5,527,907 A | 6/1996 | Or et al. |
| 5,563,135 A | 10/1996 | Hauske et al. |
| 5,563,145 A | 10/1996 | Failli et al. |
| 5,567,709 A | 10/1996 | Skotnicki et al. |
| 5,583,139 A | 12/1996 | Or et al. |
| 5,612,316 A | 3/1997 | Koch |
| 5,631,235 A | 5/1997 | Koch et al. |
| 5,648,361 A | 7/1997 | Holt et al. |
| 5,665,772 A | 9/1997 | Cottens et al. |
| 5,672,605 A | 9/1997 | Or et al. |
| 5,677,295 A | 10/1997 | Failli et al. |
| 5,935,995 A | 8/1999 | Bosslet et al. |
| 5,955,100 A | 9/1999 | Bosslet et al. |
| 5,965,160 A | 10/1999 | Benita et al. |
| 5,985,890 A | 11/1999 | Cottens et al. |
| 6,015,809 A | 1/2000 | Zhu et al. |
| 6,103,884 A | 8/2000 | Koreeda et al. |
| 6,117,863 A | 9/2000 | Zhu et al. |
| 6,146,658 A | 11/2000 | Bosslet et al. |
| 6,153,252 A | 11/2000 | Hossainy et al. |
| 6,187,757 B1 | 2/2001 | Clackson et al. |
| 6,197,781 B1 | 3/2001 | Guitard et al. |
| 6,200,985 B1 | 3/2001 | Cottens et al. |
| 6,277,983 B1 | 8/2001 | Shaw et al. |
| RE37,421 E | 10/2001 | Holt et al. |
| 6,342,507 B1 | 1/2002 | Naicker et al. |
| 6,399,626 B1 | 6/2002 | Zhu |
| 6,455,518 B1 | 9/2002 | Zenke et al. |
| 6,641,611 B1 * | 11/2003 | Jayaraman ............... 623/1.42 |
| 6,670,355 B1 | 12/2003 | Azrolan et al. |
| 6,884,429 B1 * | 4/2005 | Koziak et al. ........... 424/423 |

FOREIGN PATENT DOCUMENTS

| | | |
|---|---|---|
| WO | WO92/05179 | 4/1992 |
| WO | WO96/041807 | 12/1996 |

* cited by examiner

*Primary Examiner*—Elli Peselev
(74) *Attorney, Agent, or Firm*—Susan Sutterfield Wilks

(57) ABSTRACT

This invention provides modified rapamycins that have specific monosaccharide(s), oligosaccharide(s), pseudosugar(s) or derivatives thereof attached through a linker to create rapamycin carbohydrate derivatives having enhanced pharmacokinetic and/or pharmacodynamic profiles. For example, administration of the rapamycin carbohydrate derivative results in altered pharmacokinetic profiles and reduced toxicities. Thus, the present invention provides compounds with characteristics that are distinct from other drugs in its class such as rapamycin.

42 Claims, 12 Drawing Sheets

Figure 1: Forms of D-fructose in solution

Figure 5: *In vitro* Immunosuppressive Activity of Rapamycin 42-O-(D-Fructosylcarbonyl)rapamycin, and a Carbamate-linked Analog in a Cell Proliferation Assay.
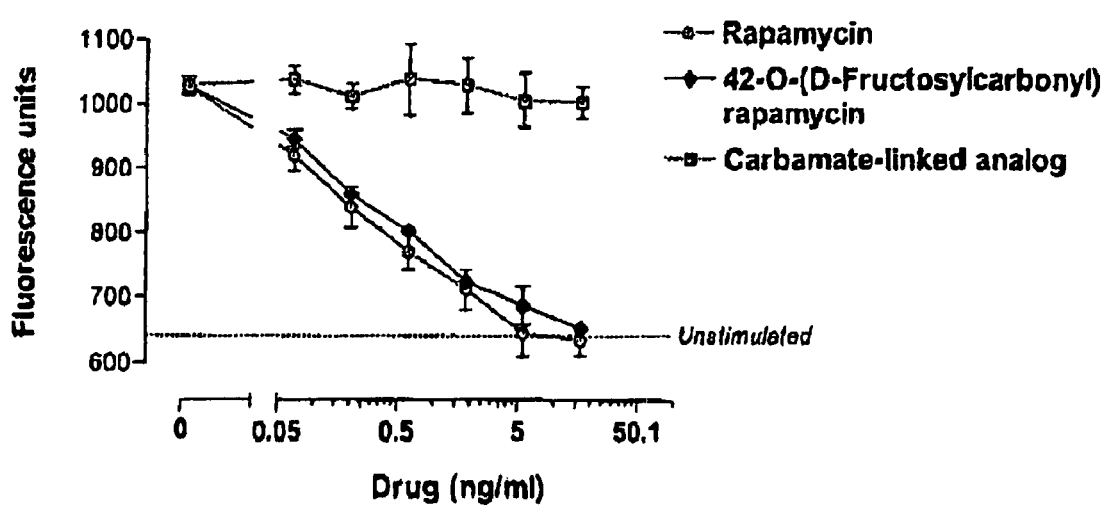

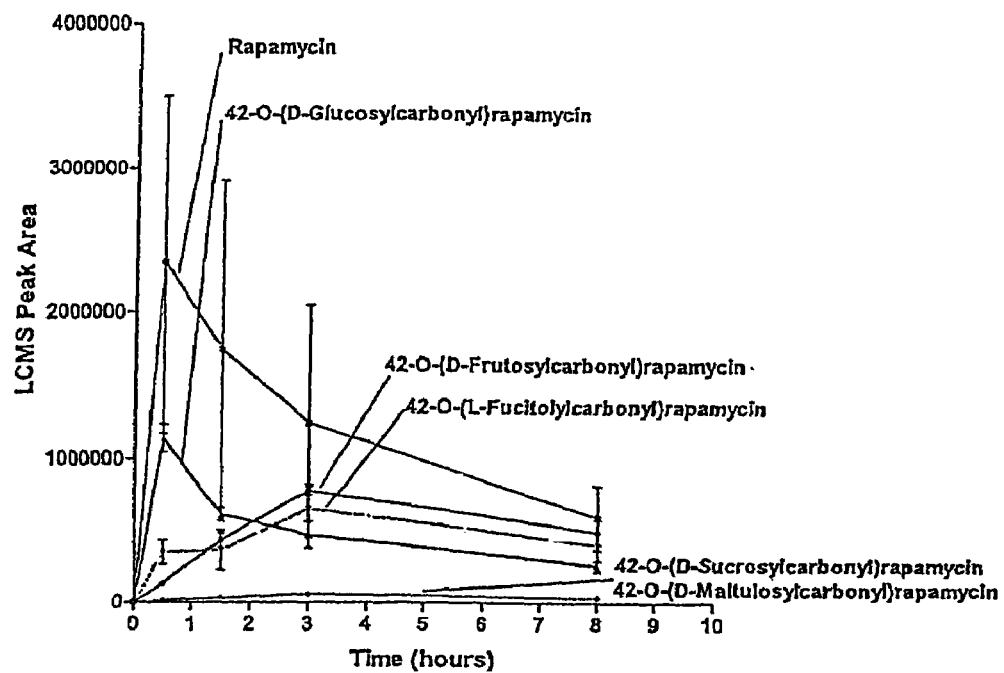
Figure 6. Pharmacokinetic Profiles in the Rat of Rapamycin-42-O-Carbohydrate Derivatives Figure 7. Pharmacokinetic Profiles in the Rat of Rapamycin-31-O-Carbohydrate Derivatives
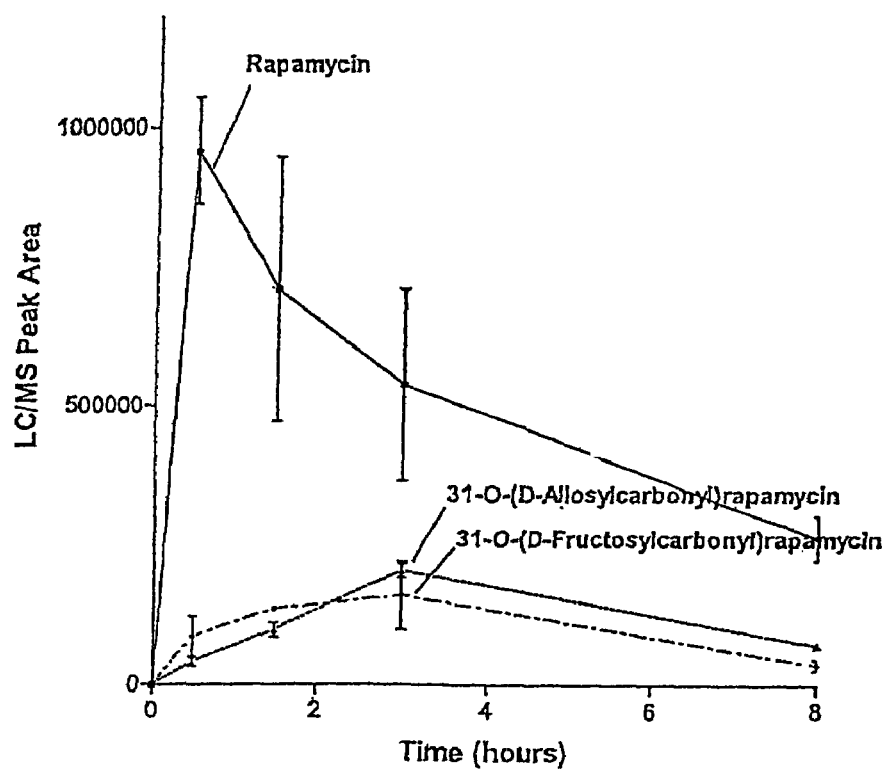

Figure 8: Pharmacokinetic Profiles in the Rat of Rapamycin-42-O-Carbohydrate Derivatives
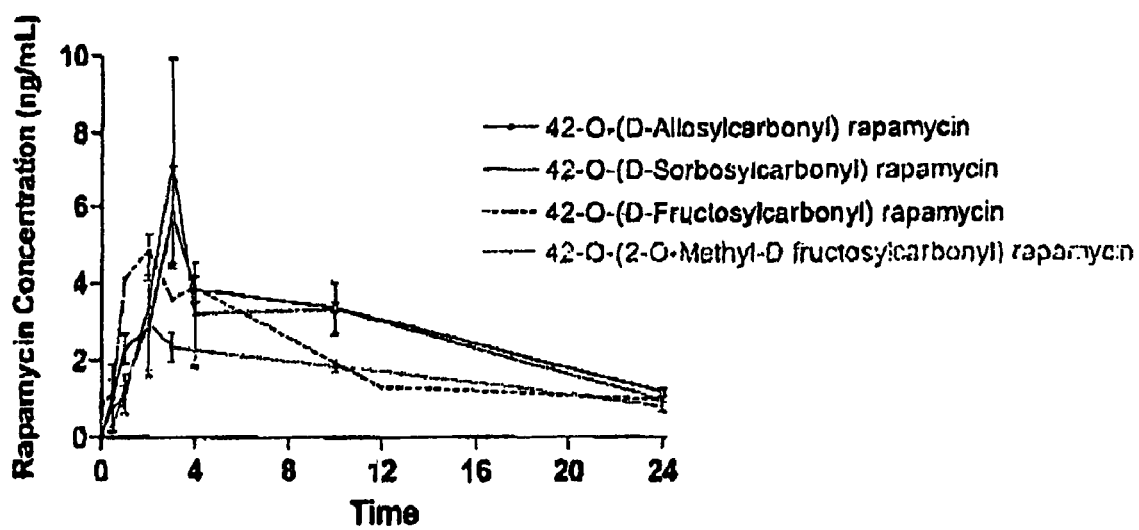

Figure 9: Serum Cholesterol Levels Following 12-Day Dosing of 42-O-(D-Fructosylcarbonyl)rapamycin and Rapamycin in Sprague-Dawley Rats
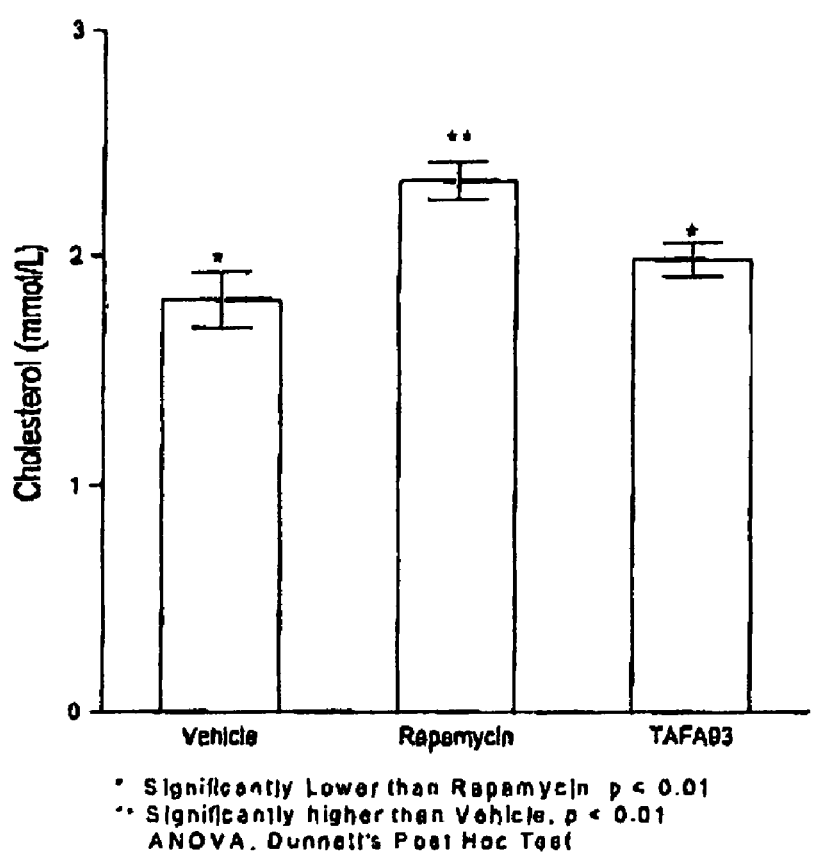

Figure 10: Dose-Response Relationship of ADP-Induced Platelet Aggregation in the Presence of 1 and 25 µg/ml Rapamycin
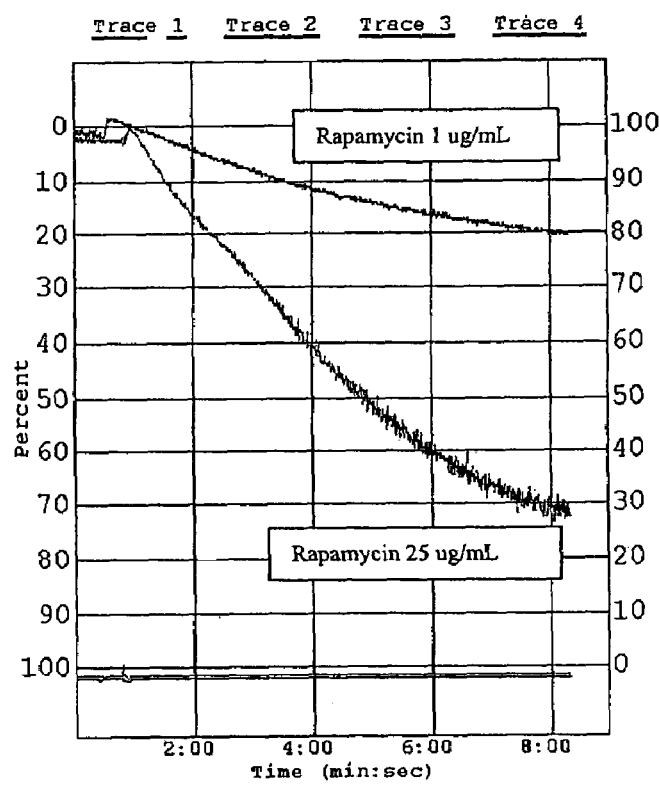

Figure 11: Effect of Rapamycin and 42-O-(D-Fructosylcarbonyl)rapamycin (25 μg/ml) on ADP-Induced Platelet Aggregation
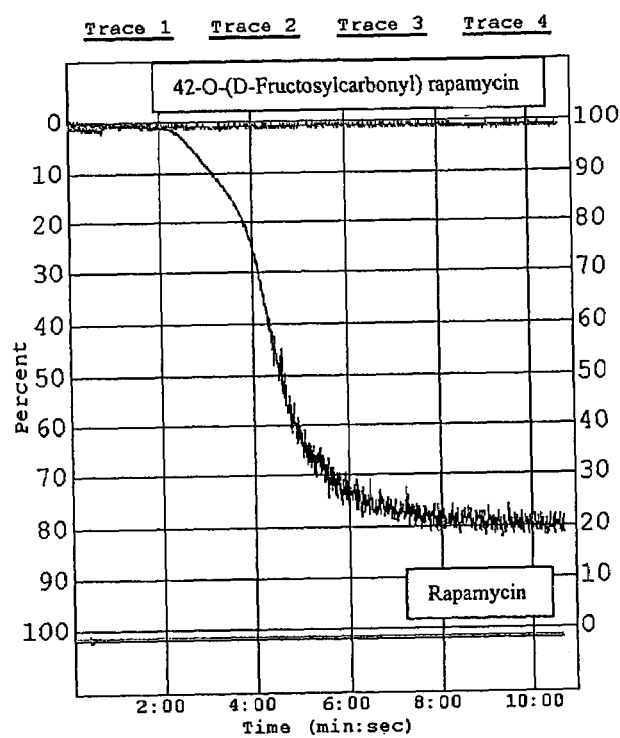

Figure 12    Graft Survival Curves of Heterotopic Heart Allografts in Rats Receiving Oral 42-O-(D-Fructosylcarbonyl)rapamycin (2.5 and 10 mg/kg/day), Rapamycin (2.5 mg/kg/day), or Vehicle
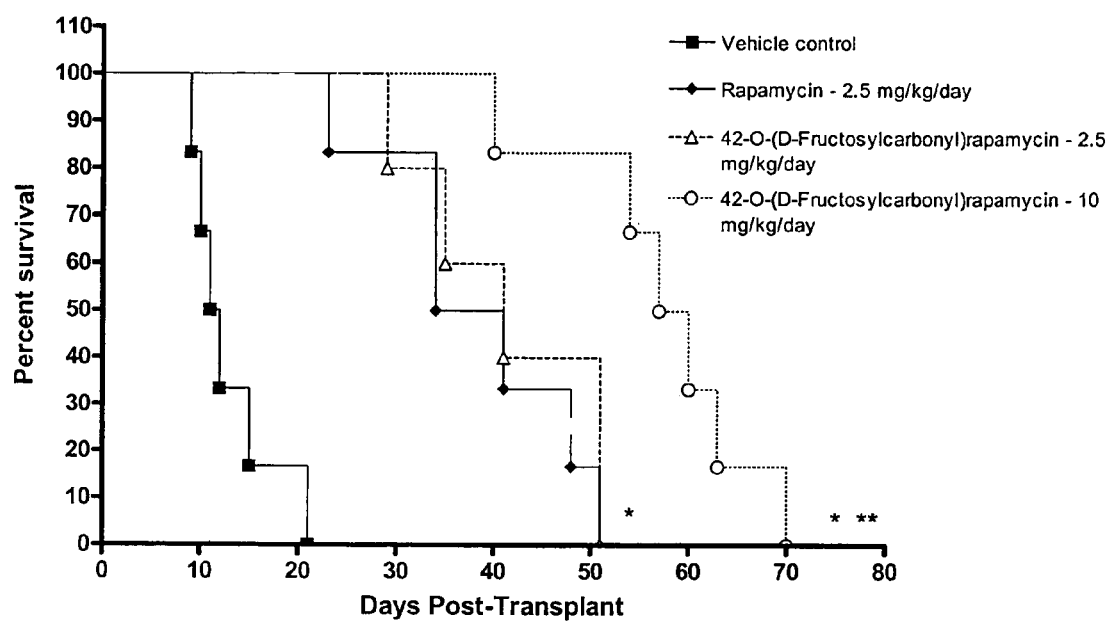
\* Different from Vehicle, $p < 0.005$
\*\* Different from Rapamycin, $p < 0.05$
   Wilcoxon Rank Sum

RAPAMYCIN CARBOHYDRATE DERIVATIVES

CROSS REFERENCE TO RELATED APPLICATIONS

This application claims the benefit of U.S. application Ser. No. 60/471,367 filed May 16, 2003, Ser. No. 60/546,240 filed Feb. 20, 2004 and Ser. No. 60/562,840 filed Apr. 16, 2004.

FIELD OF THE INVENTION

This application relates to carbohydrate derivatives of rapamycin, a potent immunosuppressant, with structurally defined carbohydrate moieties attached to the rapamycin structure via a connective moiety. The rapamycin carbohydrate derivatives may act as prodrugs. That is, they may be substantially without immunosuppressive activity themselves, but in vivo be converted to rapamycin which then exhibits an immunosuppressive effect.

REFERENCES

The following references are related hereto or referred to herein by patent or application number or by author and year at the relevant portions of this specification.

C. Vezina, A. Kiudelski, S. N. Sehgal, "Rapamycin (AY-22,989), a new antifungal antibiotic. I. Taxonomy of the producing streptomycete and isolation of the active principle," J. Antibiot. 28, 721 (1975).

S. N. Sehgal H. Baker, C. Vezina, "Rapamycin (AY-22, 989), a new antifungal antibiotic. II. Fermentation, isolation and characterization," J. Antibiot. 28, 727 (1975).

H. A. Baker, A. Sidorowicz, S. N. Sehgal, C. Vezina, "Rapamycin (AY-22,989), a new antifungal antibiotic. III. In vitro and in vivo evaluation," J. Antibiot. 31, 539 (1978).

R. Martel, J. Klicius, S. Galet, "Inhibition of the immune response by rapamycin, a new anifungal antibiotic," Can. J. Physiol. Pharmacol. 55, 48 (1977).

R. Y. Calne et al., Lancet 1183 (1978).

S. N. Sehgal, K. Molnar-Kimber, T. D. Ocain, B. M. Weichman, "Rapamycin: a novel immunosuppressive macrolide," Medicinal Research Reviews 14, 1 (1994).

F. Streit, U. Christians, H. M. Schiebel, A. Meyer, K. F. Sewing, "Structural identification of three metabolites and a degradation product of the macrolide immunosuppressant sirolimus (rapamycin) by electrospria-MS/MS after incubation with human liver microsomes," Drug Metabol. Disp., 24, 1272 (1996).

F. Streit, U. Christians, H. M. Schiebel, K. L. Napoli, L. Ernst, A. Linck, B. D. Kahan, K. F. Sewing, "Sensitive and specific quantification of sirolimus (rapamycin) and its metabolites in blood of kidney graft recipients by HPLC/electrospray-mass spectrometry," Clin. Chem. 42, 1417 (1996).

S. Miura, "Regulation of monosaccharide transporter proteins in the small intestine," Journal of Gastroenterology 37, 491 (2002).

Chem Sources USA and Chem Sources International; t e ACD electronic database; and Chemical Abstracts).

Advanced Organic Chemistry, Jerry March, John Wiley & Sons.

C. K. Wang et al., Proceedings of the 41st ASMS Conference on Mass Spectrometry and Allied Topics, San Francisco, 545 (1993).

M. J. M. Nickmilder, D. Latinne, R. K. Verbeeck, W. Janssens, D. Swoboda, G. J. Lhoest, "Isolation and identification of new rapamycin dihydrodiol metabolites from dexamethasone-induced rat liver microsomes," Xenobiotica, 27, 869 (1997).

U.S. Pat. No. 3,929,992.
U.S. Pat. No. 3,993,749.
U.S. Pat. No. 4,885,171.
U.S. Pat. No. 4,401,653.
U.S. Pat. No. 4,316,885.
U.S. Pat. No. 4,650,803.
PCT application No. WO 92/05179.
U.S. Pat. No. 5,118,678.
U.S. Pat. No. 5,260,300.
U.S. Pat. No. 5,118,678.
U.S. Pat. No. 5,118,678.
U.S. Pat. No. 5,118,678.
U.S. Pat. No. 5,100,883.
U.S. Pat. No. 5,151,413.
U.S. Pat. No. 5,120,842.
U.S. Pat. No. 5,120,725.
U.S. Pat. No. 5,120,727.
U.S. Pat. No. 5,258,389.
U.S. Pat. No. 5,672,605.
U.S. Pat. No. 5,583,139.
U.S. Pat. No. 5,527,907.
U.S. Pat. No. 5,457,111.
U.S. Pat. No. 5,955,100.
U.S. Pat. No. 6,146,658.
U.S. Pat. No. 5,935,995.
U.S. Pat. No. 5,665,728.
U.S. Pat. No. 6,146,658.

BACKGROUND OF THE INVENTION

Rapamycin, also known as sirolimus, is a 31-membered macrolide lactone, $C_{51}H_{79}NO_{13}$, with a molecular mass of 913.6 Da. In solution, rapamycin forms conformational trans- and cis-isomers with a ratio of 4:1 (in chloroform solution) due to hindered rotation around the pipecolic acid amide bond. It is sparingly soluble in water, aliphatic hydrocarbons and diethyl ether, whereas it is soluble in alcohols, halogenated hydrocarbons and dimethyl sulfoxide. Rapamycin is unstable in solution; it degrades in plasma and in low and neutral pH buffers at 37° C. with a half-life of less than 10 hours.

Produced by Streptomyces hygroscopicus, rapamycin has been shown to possess a number of valuable pharmacological attributes. The compound is a macrocyclic triene antibiotic that possesses antifungal activity, particularly against Candida albicans, both in vitro and in vivo. See, C. Vezina et al., J. Antibiot. 28, 721 (1975), S. N. Sehgal et al., J. Antibiot. 28, 727 (1975), H. A. Baker et al., J. Antibiot. 31, 539 (1978), and U.S. Pat. Nos. 3,929,992; and 3,993,749. Rapamycin alone (U.S. Pat. No. 4,885,171) or in combination with picibanil (U.S. Pat. No. 4,401,653) has also been shown to have antitumor activity. Futhermore, R. Martel et al. Can. J. Physiol. Pharmacol. 55, 48 (1977) disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989). Rapamycin, Cyclosporin A, FK-506 (also known as tacrolimus), and other macrocyclic molecules, have been shown to be effective immunosuppressive agents and therefore are useful in preventing transplant rejection. See, FASEB 3, 3411 (1989), FASEB 3, 5256 (1989), and R. Y. Calne et al., *Lancet* 1183 (1978). Although rapamycin shares structural homology with the immunosuppressant tacrolimus (FK506) and binds to the same intracellular binding protein in lymphocytes, rapamycin and tacrolimus have been shown to have different mechanisms of immunospressive action. Rapamycin inhibits S6p70-kinase whereas Tacrolimus inhibits calcineurin. Rapamycin was found to prolong graft survival of different transplants in several species alone or in combination with other immunosuppressants. See, S. N. Sehgal et al., *Medicinal Research Reviews* 14, 1 (1994).

Rapamycin is also known as an mTOR inhibitor. These inhibitors are a class of immunosuppressive drugs that inhibit T cell activation at a later stage in the immune response than other types of inhibitors like calcineurin inhibitors and DNA synthesis inhibitors. In transplantation, mTOR inhibitors are typically used in combination with calcineurin inhibitors.

Unfortunately, the side effects (e.g., gastrointestinal effects, hyperlipidemia) of mTOR inhibitors currently limit their broader use in transplantation and the treatment of autoimmune diseases. And, while not having been shown to induce nephrotoxicity, rapamycin has been shown to induce a number of toxic side effects in animal model. Such toxic effects include, for example, impairment of glucose homeostasis, gastrointestinal tract ulceration, weight loss, diarrhea and thrombocytopenia.

Numerous rapamycin derivatives have been synthesized in the hopes of alleviating and improving some drawbacks that rapamycin retains, which include low and/or variable bioavailability and solubility, and high toxicity. Mono- and diacylated derivatives of rapamycin (esterified at the 28 and 43 positions) have been shown to be useful as antifungal agents (U.S. Pat. No. 4,316,885) and used to make water soluble prodrugs (U.S. Pat. No. 4,650,803). Other derivatives include, carboxylic acid esters (PCT Publication No. WO 92/05179), carbamates (U.S. Pat. No. 5,118,678), carbonates (U.S. Pat. No. 5,260,300), amide esters (U.S. Pat. No. 5,118,678), fluorinated esters (U.S. Pat. No. 5,100,883), acetals (U.S. Pat. No. 5,151,413), silyl ethers (U.S. Pat. No. 5,120,842), bicyclic derivatives (U.S. Pat. No. 5,120,725), rapamycin dimers (U.S. Pat. No. 5,120,727) and O-aryl, O-alkyl, O-alkenyl and O-alkynyl derivatives (U.S. Pat. No. 5,258,389). Various rapamycin prodrugs have also been developed (U.S. Pat. Nos. 5,672,605, 5,583,139, 5,527,907, 5,457,111, 5,955,100, 6,146,658, and 5,935,995).

As rapamycin has been shown to possess excellent immunosuppressant, antifungal, antitumor, and other important biological activities, a need still exists for improved derivatives that increase solubility and improve the pharmakokinetic profile while decreasing its toxicity. The present invention addresses these needs.

SUMMARY OF THE INVENTION

The present invention is based in part on the recognition that carbohydrate derivatives of rapamycin in which the rapamycin molecule is modified at the 31- and/or 42-position, as defined by the current Chemical Abstracts nomenclature, by attaching monosaccharide(s), oligosaccharide(s) or pseudosugars, have similar or enhanced pharmacokinetic and/or pharmacodynamic profiles compared to rapamycin. In addition, administration of the rapamycin carbohydrate derivatives may result in reduced toxicity with retention of the desired pharmacological effect. In addition, the rapamycin carbohydrate derivatives may render rapamycin more water soluble allowing for simplified drug formulation. Thus, the present invention provides compounds with characteristics that are distinct from other drugs in its class such as rapamycin.

In one aspect, the invention is directed to a rapamycin carbohydrate derivative having the structure of formula (I):

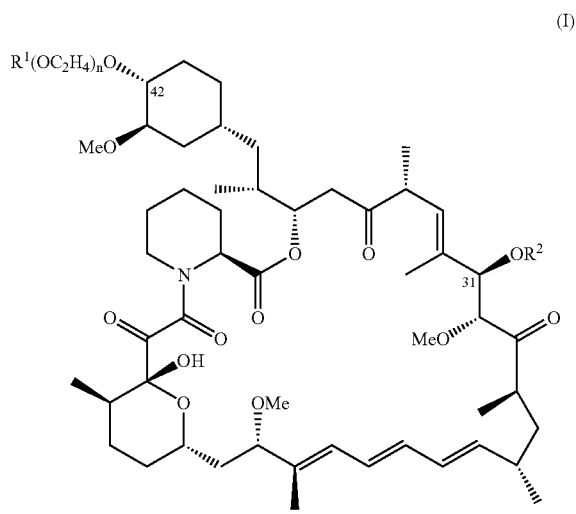

(I)

wherein n=0 or 1, $R^1$ and $R^2$ are independently hydrogen or —X—Z, wherein each X is a linker, and each Z is a carbohydrate moiety independently selected from the group consisting of a monosaccharide, an oligosaccharide and a pseudosugar wherein Z is attached to X through a hydroxyl oxygen atom of Z with the proviso that $R^1$ and $R^2$ are not both hydrogen. In an embodiment, $R^1$ can be hydrogen and $R^2$ can be X—Z or in another embodiment, $R^2$ is hydrogen and $R^1$ is X—Z. In a further embodiment, X can be selected from the group consisting of (i) —$R^3$C(O)—; (ii) —C(O)$R^3$—; iii) —$R^3$S(O)$_2$—; and (iv) —S(O)$_2R^3$—; wherein $R^3$ is selected from the group consisting of: (a) —(CH$_2$)$_p$— where p is an integer from 1 to 18; (b) —(CH$_2$)$_n$—O—(CH$_2$)$_m$— where n and m are each independently an integer from 2 to 6; and (c) a bond. In another embodiment, X can be selected from the group consisting of —C(O)— and —SO$_2$—. In an additional embodiment, X can be a single functional group. In another aspect, Z can be selected from the group consisting of fructose, fucitol and allose. In yet a further aspect, Z can be a monosaccharide derivative wherein at least one of the hydroxyl groups of the monosaccharide is replaced with a hydrogen, an alkoxy, an alkanoate or a halogen group.

Rapamycin carbohydrate derivatives having the structure of formula I that are within the scope of this invention include, for example, those set forth below (including pharmaceutically acceptable salts thereof):

42-O-(Methyl-D-glucosylcarbonyl)rapamycin;
42-O-[2-(Methyl-D-glucosylcarbonyloxy)ethyl]rapamycin;
31-O-(Methyl-D-glucosylcarbonyl)rapamycin;
42-O-(2-Hydroxyethyl)-31-O-(methyl-D-glucosylcarbonyl)rapamycin;
42-O-(2-O-Methyl-D-fructosylcarbonyl)rapamycin;
42-O-[2-(2-O-Methyl-D-fructosylcarbonyloxy)ethyl]rapamycin;
42-O-(2-O-Methyl-L-fructosylcarbonyl)rapamycin;
42-O-[2-(2-O-Methyl-L-fructosylcarbonyloxy)ethyl]rapamycin;
31-O-(2-O-Methyl-D-fructosylcarbonyl)rapamycin;
42-O-(2-Hydroxyethyl)-31-O-(2-O-methyl-D-fructosylcarbonyl)rapamycin;
31-O-(2-O-Methyl-L-fructosylcarbonyl)rapamycin;
42-O-(2-Hydroxyethyl)-31-O-(2-O-methyl-L-fructosylcarbonyl)rapamycin;
42-O-(D-Allosylcarbonyl)rapamycin;
42-O-[2-(D-Allosylcarbonyloxy)ethyl]rapamycin;
42-O-(L-Allosylcarbonyl)rapamycin;
42-O-[2-(L-Allosylcarbonyloxy)ethyl]rapamycin;
31-O-(D-Allosylcarbonyl)rapamycin;
42-O-(2-Hydroxyethyl)-31-O-(D-allosylcarbonyl)rapamycin;
31-O-(L-Allosylcarbonyl)rapamycin;
42-O-(2-Hydroxyethyl)-31-O-(L-allosylcarbonyl)rapamycin;
42-O-(D-Fructoslylcarbonyl)rapamycin;
42-O-[2-(D-Fructoslylcarbonyloxy)ethyl]rapamycin;
42-O-(L-Fructoslylcarbonyl)rapamycin;
42-O-[2-(L-Fructoslylcarbonyloxy)ethyl]rapamycin;
31-O-(D-Fructoslylcarbonyl)rapamycin;
42-O-(2-Hydroxyethyl)-31-O-(D-fructoslylcarbonyl)rapamycin;
31-O-(L-Fructoslylcarbonyl)rapamycin;
42-O-(2-Hydroxyethyl)-31-O-(L-fructoslylcarbonyl)rapamycin;
42-O-(D-Fucitolylcarbonyl)rapamycin;
42-O-[2-(D-Fucitolylcarbonyloxy)ethyl]rapamycin;
42-O-(L-Fucitolylcarbonyl)rapamycin;
42-O-[2-(L-Fucitolylcarbonyloxy)ethyl]rapamycin;
31-O-(D-Fucitolylcarbonyl)rapamycin;
42-O-(2-Hydroxyethyl)-31-O-(D-fucitolylcarbonyl)rapamycin;
31-O-(L-Fucitolylcarbonyl)rapamycin;
42-O-(2-Hydroxyethyl)-31-O-(L-fucitolylcarbonyl)rapamycin;
42-O-(D-Glucalylcarbonyl)rapamycin;
42-O-[2-(D-Glucalylcarbonyloxy)ethyl]rapamycin;
42-O-(D-Glucosylcarbonyl)rapamycin;
42-O-[2-(D-Glucosylcarbonyloxy)ethyl]rapamycin;
42-O-(L-Glucosylcarbonyl)rapamycin;
42-O-[2-(L-Glucosylcarbonyloxy)ethyl]rapamycin;
31-O-(D-Glucalylcarbonyl)rapamycin;
42-O-(2-Hydroxyethyl)-31-O-(D-glucalylcarbonyl)rapamycin;
31-O-(D-Glucosylcarbonyl)rapamycin;
42-O-(2-Hydroxyethyl)-31-O-(D-glucosylcarbonyl)rapamycin;
31-O-(L-Glucosylcarbonyl)rapamycin;
42-O-(2-Hydroxyethyl)-31-O-(L-glucosylcarbonyl)rapamycin;
42-O-(L-Sorbosylcarbonyl)rapamycin;
42-O-(D-Sorbosylcarbonyl)rapamycin;
31-O-(L-Sorbosylcarbonyl)rapamycin;
31-O-(D-Sorbosylcarbonyl)rapamycin;
42-O-[2-(L-Sorbosylcarbonyloxy)ethyl]rapamycin;
42-O-[2-(D-Sorbosylcarbonyloxy)ethyl]rapamycin;
42-O-(2-Hydroxyethyl)-31-O-(D-sorbosylcarbonyl)rapamycin;
42-O-(2-Hydroxyethyl)-31-O-(L-sorbosylcarbonyl)rapamycin;
42-O-(D-Lactalylcarbonyl)rapamycin;
42-O-[2-(D-Lactalylcarbonyloxy)ethyl]rapamycin;
31-O-(D-Lactalylcarbonyl)rapamycin;
42-O-(2-Hydroxyethyl)-31-O-(D-lactalylcarbonyl)rapamycin;
42-O-(D-Sucrosylcarbonyl)rapamycin;
42-O-[2-(D-Sucrosylcarbonyloxy)ethyl]rapamycin;
31-O-(D-Sucrosylcarbonyl)rapamycin;
42-O-(2-Hydroxyethyl)-31-O-(D-sucrosylcarbonyl)rapamycin;
42-O-(D-Gentobiosylcarbonyl)rapamycin
42-O-[2-(D-Gentobiosylcarbonyloxy)ethyl]rapamycin;
31-O-(D-Gentobiosylcarbonyl)rapamycin
42-O-(2-Hydroxyethyl)-31-O-(D-gentobiosylcarbonyl)rapamycin
42-O-(D-Cellobiosylcarbonyl)rapamycin;
42-O-[2-(D-Cellobiosylcarbonyloxy)ethyl]rapamycin;
31-O-(D-Cellobiosylcarbonyl)rapamycin;
42-O-(2-Hydroxyethyl)-31-O-(D-cellobiosylcarbonyl)rapamycin;
42-O-(D-Turanosylcarbonyl)rapamycin;
42-O-[2-(D-Turanosylcarbonyloxy)ethyl]rapamycin;
31-O-(D-Turanosylcarbonyl)rapamycin;
42-O-(2-Hydroxyethyl)-31-O-(D-turanosylcarbonyl)rapamycin;
42-O-(D-Palatinosylcarbonyl)rapamycin;
42-O-[2-(D-Palatinosylcarbonyloxy)ethyl]rapamycin;
31-O-(D-Palatinosylcarbonyl)rapamycin;
42-O-(2-Hydroxyethyl)-31-O-(D-palatinosylcarbonyl)rapamycin;
42-O-(D-Isomaltosylcarbonyl)rapamycin;
42-O-[2-(D-Isomaltosylcarbonyloxy)ethyl]rapamycin;
31-O-(D-Isomaltosylcarbonyl)rapamycin;
42-O-(2-Hydroxyethyl)-31-O-(D-isomaltosylcarbonyl)rapamycin;
42-O-(D-Maltulosylcarbonyl)rapamycin;
42-O-[2-(D-Maltulosylcarbonyloxy)ethyl]rapamycin;
42-O-(D-Maltosylcarbonyl)rapamycin;
42-O-[2-(D-Maltosylcarbonyloxy)ethyl]rapamycin;
31-O-(D-Maltulosylcarbonyl)rapamycin;
42-O-(2-Hydroxyethyl)-31-O-(D-maltulosylcarbonyl)rapamycin;
31-O-(D-Maltosylcarbonyl)rapamycin;
42-O-(2-Hydroxyethyl)-31-O-(D-maltosylcarbonyl)rapamycin;
42-O-(D-Lactosylcarbonyl)rapamycin;
42-O-[2-(D-Lactosylcarbonyloxy)ethyl]rapamycin;
31-O-(Methyl-D-lactosylcarbonyl)rapamycin;
42-O-(2-Hydroxyethyl)-31-O-(methyl-D-lactosylcarbonyl)rapamycin;
42-O-(D-Melibiosylcarbonyl)rapamycin;
31-O-(D-Melibiosylcarbonyl)rapamycin;
42-O-(2-Hydroxyethyl)-31-O-(D-melibiosylcarbonyl)rapamycin;
42-O-(D-Leucrosylcarbonyl)rapamycin;
42-O-[2-(D-Leucrosylcarbonyloxy)ethyl]rapamycin;
31-O-(D-Leucrosylcarbonyl)rapamycin;
42-O-(2-Hydroxyethyl)-31-O-(D-leucrosylcarbonyl)rapamycin;
42-O-(D-Rafinosylcarbonyl)rapamycin;
42-O-[2-(D-Rafinosylcarbonyloxy)ethyl]rapamycin;

31-O-(D-Rafinosylcarbonyl)rapamycin;
42-O-(2-Hydroxyethyl)-31-O-(D-rafinosylcarbonyl)rapamycin;
42-O-(D-Isomaltotriosylcarbonyl)rapamycin;
42-O-[2-(D-Isomaltosylcarbonyloxy)ethyl]rapamycin;
31-O-(D-Isomaltotriosylcarbonyl)rapamycin;
42-O-(2-Hydroxyethyl)-31-O-(D-isomaltotriosylcarbonyl)rapamycin;
42-O-(D-Cellotetraosylcarbonyl)rapamycin;
42-O-[2-(D-Cellotetraosylcarbonyloxy)ethyl]rapamycin;
31-O-(D-Cellotetraosylcarbonyl)rapamycin;
42-O-(2-Hydroxyethyl)-31-O-(D-cellotetraosylcarbonyl)rapamycin;
42-O-(Valiolylcarbonyl)rapamycin
42-O-[2-(D-Valiolylcarbonyloxy)ethyl]rapamycin;
31-O-(Valiolylcarbonyl)rapamycin
42-O-(2-Hydroxyethyl)-31-O-(valiolylcarbonyl)rapamycin
42-O-(Valiolonylcarbonyl)rapamycin
42-O-[2-(D-Valiolonylcarbonyloxy)ethyl]rapamycin;
31-O-(Valiolonylcarbonyl)rapamycin
42-O-(2-Hydroxyethyl)-31-O-(valiolonylcarbonyl)rapamycin
42-O-(Valienolylcarbonyl)rapamycin
42-O-[2-(D-Valienolylcarbonyloxy)ethyl]rapamycin;
31-O-(Valienolylcarbonyl)rapamycin
42-O-(2-Hydroxyethyl)-31-O-(valienolylcarbonyl)rapamycin
42-O-(Valienoneylcarbonyl)rapamycin
42-O-[2-(D-Valienoneylcarbonyloxy)ethyl]rapamycin;
31-O-(Valienoneylcarbonyl)rapamycin
42-O-(2-Hydroxyethyl)-31-O-(valienoneylcarbonyl)rapamycin In another aspect, the invention is directed to a pharmaceutical composition comprising the aforementioned rapamycin carbohydrate derivative, or a pharmaceutically acceptable salt thereof, and a pharmaceutically acceptable carrier. In addition, an embodiment of the invention is a method for treating a disease treatable by rapamycin by administering a therapeutically effective amount of the rapamycin carbohydrate derivative to a subject in need thereof.

In yet another aspect of the current invention, a method is presented for treating a condition such as transplantation rejection, host vs. graft disease, graft vs. host disease, leukemia, lymphoma, hyperproliferative vascular disorders, autoimmune disease, diseases of inflammation, solid tumors, and fungal infections in a patient, said method comprising administering a therapeutically effective amount of the aforementioned pharmaceutical composition to a patient in need thereof.

Still further, the invention provides a medical device where the medical device comprises a rapamycin carbohydrate derivative or a pharmaceutically acceptable salt thereof. In an embodiment, the device is coated with the rapamycin carbohydrate derivative.

And, the invention provides a method for treating a disease treatable by rapamycin, comprising coadministering a therapeutically effective amount of a rapamycin carbohydrate derivative of the present invention to a subject in need thereof with a pharmaceutical composition selected from the group consisting of a cyclosporine or cyclosporine derivative, a steroid, or an immunomodulatory compound.

BRIEF DESCRIPTION OF THE DRAWINGS

FIG. 5 depicts the in vitro immunosuppressive activity of rapamycin, 42-O-(D-fructosylcarbonyl)rapamycin and a carbamate-linked analog of 42-O-(D-fructosylcarbonyl)rapamycin.

FIGS. 6, 7 and 8 depict pharmacokinetic profiles of selected rapamycin carbohydrate derivatives in rats.

FIG. 9 depicts serum cholesterol levels in rats following treatment with 42-O-(D-fructosylcarbonyl)rapamycin and rapamycin.

FIG. 10 shows the effect of two different doses of rapamycin on platelet aggregation.

FIG. 11 compares the effect of 42-O-(D-fructosylcarbonyl)rapamycin and rapamycin on platelet aggregation.

FIG. 12 illustrates the effect of 42-O-(D-fructosylcarbonyl)rapamycin and rapamycin on survival rates in a rat heart transplant model.

DETAILED DESCRIPTION OF THE INVENTION

Figure 1:
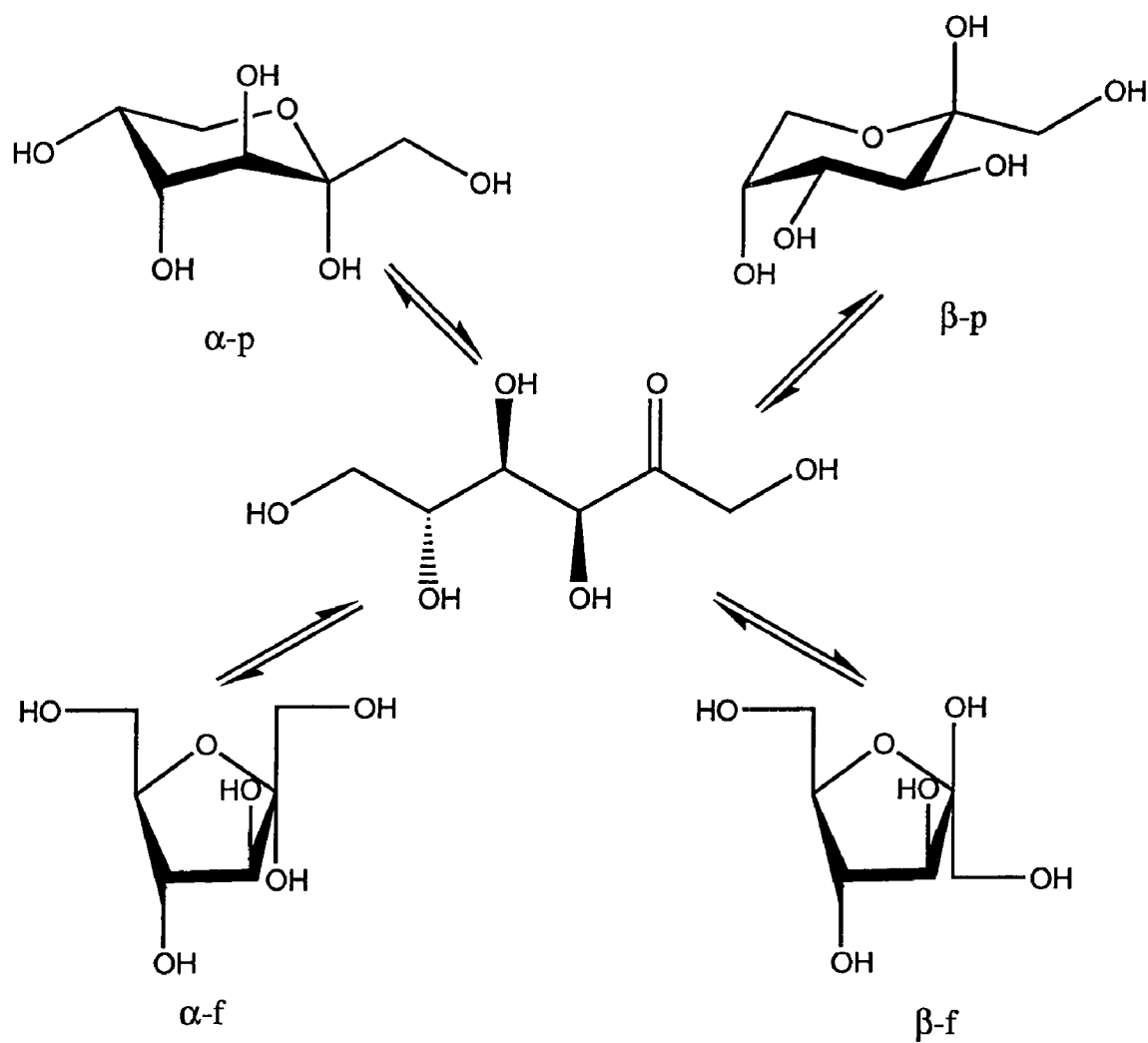
FIG. 1 depicts fructose as it exists in several configurations in solution

This invention relates to the unexpected discovery that the claimed rapamycin carbohydrate derivatives have improved pharmacological properties as compared to underivatized rapamycin.

It must be noted that as used herein and in the appended claims, the singular forms "a," "an," and "the" include plural references unless context clearly dictates otherwise. Thus, for example, a reference to "a rapamycin carbohydrate derivative" includes a plurality of such derivatives; a reference to a "pharmaceutically acceptable carrier" is a reference to one or more carriers and to equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described.

All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, immunology and pharmacology, within the skill of the art. Such techniques are explained fully in the literature. (See, e.g., Gennaro, A. R., ed. (1990) Remington's Pharmaceutical Sciences, 18th ed., Mack Publishing Co.; Colowick, S. et al., eds., Short Protocols in Molecular Biology, 4th edition, John Wiley & Sons; Ream et al., eds. (1998) Molecular Biology Techniques: An Intensive Laboratory Course, Academic Press).

Definitions

When discussing rapamycin carbohydrate derivatives, compositions, or methods, the following terms have the following meanings unless otherwise indicated. Undefined terms have their art-recognized meanings.

The term "alkyl" refers to alkyl groups having from 1 to 10 carbon atoms, for example 1 to 6 carbon atoms, and includes both straight chain and branched chain alkyl groups. This term is exemplified by groups such as methyl, t-butyl, n-heptyl, octyl and the like.

The term "alkene" refers to an unsaturated alkyl group having at least one point of alkene unsaturation (i.e. —C═C—) and further having from 1 to 10 carbon atoms, for example from 1 to 6 carbon atoms, and includes both straight chain and branched chain alkyl groups.

The term "alkyne" refers to an unsaturated alkyl group having at least one point of alkyne unsaturation (i.e. —C≡C—) and further having from 1 to 10 carbon atoms, for example from 1 to 6 carbon atoms, and includes both straight and branched chain alkyl groups.

The term "aromatic" group refers to an aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like).

The term "protecting group" or "blocking group" refers to any group which, when bound to one or more hydroxyl group(s) of rapamycin or a sugar moiety, prevents reactions from occurring at these hydroxyl group(s) and which protecting groups can be removed by conventional chemical or enzymatic steps to reestablish the hydroxyl group(s). The particular removable protecting group employed is determined by the nature of the compounds and chemical processes being utilized. Removable hydroxyl blocking groups include conventional substituents such as allyl, benzyl, acetyl, chloroacetyl, thiobenzyl, benzylidene, phenacyl, t-butyldimethylsilyl and trialkylsilyls such as triethylsilyl, triisopropylsilyl, trimethylsily, tributylsilyl and the like, and any other group that can be introduced chemically onto a hydroxyl functionality and later selectively removed either by chemical or enzymatic methods in mild conditions compatible with the nature of the product.

The Rapamycin Carbohydrate Derivatives

As discussed above, the rapamycin carbohydrate derivatives of the invention are compounds having the structure of formula (I):

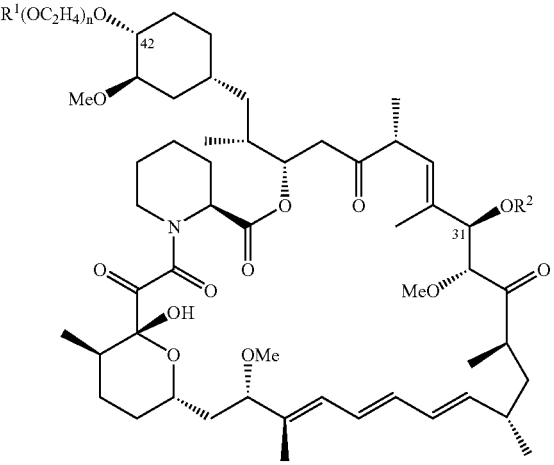

(I)

wherein n=0 or 1, $R^1$ and $R^2$ are independently hydrogen or—X—Z, wherein each X is a linker, and each Z is a carbohydrate moiety independently selected from the group consisting of a monosaccharide, oligosaccharide and pseudosugar, with the proviso that $R^1$ and $R^2$ are not both hydrogen.

As will be evident, the rapamycin derivatives can have sugar derivative moieties attached at the 42-position, the 31-position, or both the 42- and the 31-positions. In one embodiment, the sugar derivative is attached at the 42-position alone and in another embodiment the sugar derivative is attached at the 31-position alone.

It is important to note that in naturally-occurring rapamycin, the 41-methoxy and 42-hydroxy substituents exist in a trans configuration relative to each other. The 42-O-(glycosylcarbonyl)rapamycin compounds of the present invention are prepared in such a way as to retain the trans configuration of the 41- and 42-substituents. Consequently, upon hydrolysis of the carbonate linkage, the rapamycin will be released in its naturally-occurring configuration. Similarly, the 31-O-(glycosylcarbonyl)rapamycin compounds of the present invention are prepared in such a way as to retain the naturally-occurring stereochemistry of the 31-hydroxyl substitutent of rapamycin.

The Carbohydrate Moiety

The carbohydrate (or sugar) moiety, represented by the identifier "Z" in formula (I), is formed from a monosaccharide, oligosaccharide, pseudosugar or derivative thereof having a reactive functional group that can be coupled (i) directly to the hydroxyl group(s) at either or both of the 31- and 42-positions of rapamycin or (ii) to a reactive functional group(s) on an activated rapamycin to yield a rapamycin carbohydrate derivative of the present invention. The functional group is optionally attached to a linker that in turn is attached to the sugar, typically but not necessarily at the anomeric center. Such optional linker groups are discussed further below.

The sugars that comprise the sugar derivative can differ from each other in a multitude of ways. For example, they can exist in the pyranose or furanose forms to differing degrees. Certain sugars such as fucitol exist exclusively in the open chain form whereas many others (e.g. glucose, ribose, allose) exist predominantly in the cyclic form. Physicochemical properties of the sugar such as the geometry, composition, size, flexibility or rigidity, and the relative hydrophilicity can all affect the chemical characteristics of the rapamycin carbohydrate derivative.

In solution fructose, for example, can exist mostly in a 6-membered pyranose form and/or its 5-membered furanose form. (See FIG. 1). And, each of these forms can exist in alpha or beta configurations. In addition, fructose can exist in an open-chain form. Therefore, fructose can exist in its α-fructopyranose, β-fructopyranose, α-fructofuranose or, β-fructofuranose or open chain forms as shown in FIG. 6. And, fructose can be attached to a drug in any of these configurations. In its 6-membered pyranose form, fructose is more likely to form a bond, to a drug, for example, through the single primary alcohol that is present at the 1 position in the pyranose form. In its 5-membered furanose form, fructose has two primary alcohols which are at the 1 and 6 position. In the furanose form, bonds are likely through either of these primary alcohols at the 1 or the 6 position.

The manner in which the body absorbs and processes the specific sugars varies. Many people have difficulty processing lactose, for instance. Such lactose intolerance could make the incorporation of lactose into the rapamycin carbohydrate derivative unsuitable. Further, oligosaccharides are not absorbed intact from the digestive tract and must first be digested to their monosaccharide constituents. Monosaccharides, however, are absorbed by transporter systems located in the brush border membrane of enterocytes. See, S. Miura, Journal of Gastroenterology 37, 491 (2002). For example, glucose and galactose are absorbed by the SGLT1 transporter system. Another transporter, GLUT2, facilitates mainly glucose transport, and yet another transporter known as GLUT5 transports fructose. The presence in the gastrointestinal tract of different monosaccharide transporter proteins with differing selectivities could lead to varied absorption of various rapamycin carbohydrate derivatives. That is, certain derivatives may be more readily able to take advantage of an available transporter in order to facilitate the passage of the rapamycin carbohydrate derivative out of the gastrointestinal tract and deliver it to the blood stream where the carbohydrate moiety can be cleaved off, thereby releasing rapamycin. It is believed that such a facilitated process may result in lowered gastrointestinal toxicity associated with localized exposure to rapamycin.

In view of the above, it is apparent that the appropriate selection of the carbohydrate moiety (monosaccharide, oligosaccharide, or pseudosugar) incorporated into the rapamycin carbohydrate derivative can have a major influence on the derivative's pharmacokinetic and/or pharmacodynamic properties. Accordingly, the carbohydrate moiety can be carefully chosen to optimize the pharmacokinetic and/or pharmacodynamic properties of the rapamycin carbohydrate derivative.

Suitable monosaccharides include, but are not limited to, any of several simple open or closed chain sugars (in the L or D configuration), typically having 5 or 6 carbons (a pentose monosaccharide or a hexose monosaccharide), as well as 7 carbons (heptose monosaccharide). Included are sugar derivatives in which the ring oxygen atom has been replaced by carbon, nitrogen or sulfur, amino sugars in which a hydroxyl substituent on the simple sugar is replaced with an amino group or sugars having a double bond between two adjacent carbon atoms, (e.g. glucosamine, 5-thio-D-glucose, nojirimycin, deoxynojirimycin, 1,5-anhydro-D-sorbitol, 2,5-anhydro-D-mannitol, 2-deoxy-D-galactose, 2-deoxy-D-glucose, 3-deoxy-D-glucose, allose, arabinose, arabinitol, fucitol, fucose, galactitol, glucitol, iditol, lyxose, mannitol, levo-rhamnitol, 2-deoxy-D-ribose, ribose, ribitol, ribulose, rhamnose, xylose, xylulose, allose, altrose, fructose, galactose, glucose, gulose, idose, levulose, mannose, psicose, sorbose, tagatose, talose, galactal, glucal, fucal, rhamnal, arabinal, xylal, valienamine, validamine, valiolamine, valiol, valiolon, valienol, valienone, glucuronic acid, galacturonic acid, N-acetylneuraminic acid, gluconic acid D-lactone, galactonic acid γ-lactone, galactonic acid δ-lactone, mannonic acid γ-lactone, D-altro-heptulose, D-manno-heptulose, D-glycero-D-manno-heptose, D-glycero-D-gluco-heptose, D-allo-heptulose, D-altro-3-heptulose, D-glycero-D-manno-heptitol, D-glycero-D-altro-heptitol and the like), The hydroxyl groups on monosaccharides may optionally be replaced with hydrogen, alkoxy (e.g. 2-O-methyl-D-fructose), alkanoate or halogen groups. Included are sulfate and/or phosphate derivatives of monosaccharides as defined herein.

Suitable oligosaccharides include, but are not limited to, carbohydrates having from 2 to 10 or more monosaccharides linked together. The constituent monosaccharide unit may be, for example, a pentose monosaccharide, a hexose monosaccharide, or a pseudosugar (including a pseudoaminosugar). Oligosaccharides do not include bicyclic groups that are formed by fusing a monosaccharide to a benzene ring, a cyclohexane ring, or a heterocyclic ring.

Pseudosugars that may be used in the invention are members of the class of compounds wherein the ring oxygen atom of the cyclic monosaccharide is replaced by a methylene group. Pseudosugars are also known as "carba-sugars."

The Linker

Figure 3:
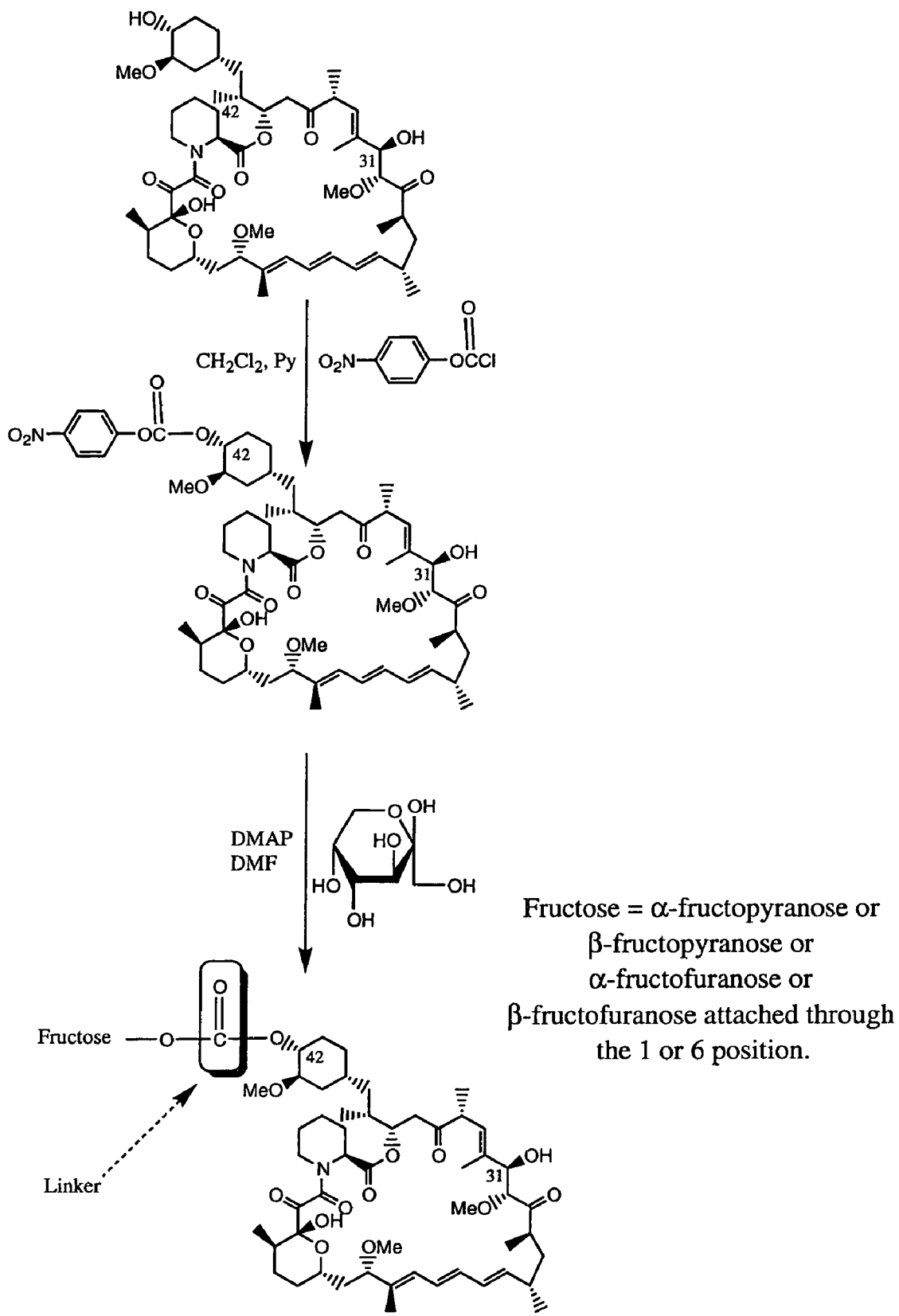
FIG. 3 depicts the reaction pathway for the synthesis of 42-O-(D-fructosylcarbonyl)rapamycin.

As discussed above, the carbohydrate moiety is covalently attached to the rapamycin via a linker, indicated as "X" in formula I. In it's simplest form, the linker is a chemical functional group that is formed when the sugar derivative is covalently attached to rapamycin, but is itself part of neither rapamycin nor the sugar molecule. In one embodiment, the nature of the linker is determined by the chemistry employed to covalently attach the sugar or sugar derivative to rapamycin. For example, if 42-O-(4-nitrophenyloxycarbonyl)rapamycin (an activated rapamycin) is reacted with a sugar the result is a rapamycin carbohydrate derivative wherein the 42-hydroxyl oxygen of rapamycin is covalently bonded to a carbonyl group which in turn is covalently bonded to a hydroxyl oxygen on the sugar. In this example, the linker is the carbonyl group (C=O). An example of a linker as defined herein is depicted in FIG. 3. Examples of linkers include moieties such as carbonyl (C=O) and sulfonyl (O=S=O). Such a carbonyl or sulfonyl linker is recognized as a single functional group linker.

The linker together with the functionality through which the sugar and rapamycin are attached to that linker form a "linkage." For example, when a carbonyl linker is attached to a sugar via one of its hydroxyl oxygen atoms and then to a rapamycin hydroxyl oxygen, the resulting "linkage" is a carbonate (i.e. —OC(O)O—). An example of a linkage as defined herein in depicted in FIG. 4. Examples of linkages include esters, ethers, carbonates, carbamates, sulfates and urethanes.

The linker and associated linkage are selected to provide a biocompatible, substantially non-immunogenic rapamycin carbohydrate derivative. While the present invention is based on the recognition that the presence of the sugar(s) will improve the effectiveness of rapamycin, its pharmacokinetic and/or pharmacodynamic properties may also be enhanced by the geometry, composition, size, flexibility or rigidity, the relative hydrophobicity or hydrophilicity, and similar properties of the linker and/or linkage. Accordingly, the linker or linkage can be chosen to optimize the pharmacokinetic and/or pharmacodynamic properties of the rapamycin carbohydrate derivative. For example, the rates of acid-catalyzed or enzymatic hydrolysis of the derivatives resulting in the release of free rapamycin will vary depending on which linkage is created. The linker or linkage may be biologically "neutral," i.e., not itself contribute any additional biological activity to the carbohydrate rapamycin derivative, or it may be chosen to further enhance the biological activity of the compound.

The reaction chemistries resulting in linkers and linkages employ conventional techniques. These techniques generally involve the use of complimentary reactive functional groups located on rapamycin or activated rapamycin and the sugar or sugar derivative. Examples of complimentary functional groups and the resulting linkages are found in Table 1.

TABLE 1

LINKAGES RESULTING FROM COMPLIMENTARY FUNCTIONALITIES

| FIRST REACTIVE GROUP | SECOND REACTIVE GROUP | LINKAGE |
|---|---|---|
| hydroxyl | isocyanate | urethane |
| amine | epoxide | β-aminohydroxy |
| sulfonyl halide | amine | sulfonamide |
| carboxyl acid | amine | amide |
| hydroxyl | alkyl/aryl halide | ether |
| aldehyde | amine/NaCNBH$_3$ | amine |
| ketone | amine/NaCNBH$_3$ | amine |
| amine | isocyanate | carbamate |
| carboxyl acid | hydroxyl | ester |
| chloroformate | hydroxyl | carbonate |

If desired, the linker may contain more than a single functional group. Complex linkers may be used to provide different chemical properties into the rapamycin carbohydrate derivative. For example, different hydrophobic/hydrophilic characteristics may be imparted to the rapamycin carbohydrate derivative by manipulation of the linker. Similarly, charged moieties may also be introduced. Techniques for modification of the linker will be readily understood by those of skill in the art. For example, the hydrophobic nature of a linker derived from hexamethylene diamine or a related polyamine can be modifed to be substantially more hydrophilic by replacing the alkylene group with a poly(oxyalkylene) group.

For example, glycosyl-Y[—C(=Y)—X—]p-W(R)n-X—C(=Y)-drug where W is an aromatic or heteroaromatic or aliphatic group with conjugated double bonds or an aminoacid derivative radical which cyclizes after elimination of the glycosyl radical was disclosed in U.S. Pat. No. 6,146,658. These complex linkers are designed to self-eliminate via cyclization subsequent to enzymatic removal of the glycosyl moiety.

Wide varieties of linkers are suitable for use in the invention. Ordinarily skilled artisans will recognize that a carbonyl (C=O) or a sulfonyl (O=S=O) linker, or a carbonyl or sulfonyl linker combined with a simple alkyl chain or a polyether chain (e.g. a small number of repeating ethylene oxide units) will have properties that are different from those of the more complex linkers described above. For example, it is contemplated that the linkers of the present invention will not undergo cyclization to self-eliminate. Further, the susceptibility of the linker/drug compound to enzymatic or hydrolytic cleavage will be highly dependent on the nature of the spacer or linker moiety. In addition, it is contemplated that compounds with complicated linkers may be more difficult and expensive to produce than compounds with only single functional group linkers, such as those of the present invention.

Wide varieties of linkers are commercially available (e.g., Chem Sources USA and Chem Sources International; the ACD electronic database; and Chemical Abstracts). Many of the linkers that are suitable for use in this invention fall into this category. Others can be readily synthesized by methods known in the art, and as described below. Examples of linkers include aliphatic moieties, aromatic moieties, steroidal moieties, peptides, and the like. Specific examples of commercially available linkers are peptides or polyamides, hydrocarbons, aromatics, heterocyclics, ethers, lipids, cationic or anionic groups, or a combination thereof.

It is contemplated that the properties of the linker of this invention can be modified by the addition or insertion of ancillary groups, for example, to change the solubility of the multibinding compound (in water, fats, lipids, biological fluids, etc.), hydrophobicity, hydrophilicity, linker flexibility, antigenicity, stability, and the like. For example, the introduction of one or more polyethylene glycol (PEG) groups onto the linker enhances the hydrophilicity and water solubility of the rapamycin carbohydrate derivative, increases both molecular weight and molecular size and, depending on the nature of the unPEGylated linker, may increase the in vivo retention time. Further, PEG may decrease antigenicity and potentially enhances the overall rigidity of the linker.

Ancillary groups that enhance the water solubility/hydrophilicity of the linker, and accordingly, the resulting compounds, are useful in practicing this invention. Thus, it is within the scope of the present invention to use ancillary groups such as, for example, small repeating units of ethylene glycols, alcohols, polyols, (e.g., glycerin, glycerol propoxylate, etc.) carboxylates (e.g., small repeating units of glutamic acid, acrylic acid, etc.), amines (e.g., tetraethylenepentamine), and the like to enhance the water solubility and/or hydrophilicity of the carbohydrate rapamycin derivatives of this invention. For example, the ancillary group used to improve water solubility/hydrophilicity may be a polyether containing a small number of repeating ethylene oxide (—CH$_2$CH$_2$O—) units.

The incorporation of lipophilic ancillary groups within the structure of the linker to enhance the lipophilicity and/or hydrophobicity of the rapamycin carbohydrate derivatives is also within the scope of this invention. Lipophilic groups useful with the linkers of this invention include, but are not limited to, lower alkyl, aromatic groups, and polycyclic aromatic groups. The aromatic groups may be either unsubstituted or substituted with other groups, but are at least substituted with a group that allows their covalent attachment to the linker. As used herein the term "aromatic groups" incorporates both aromatic hydrocarbons and heterocyclic aromatics. Other lipophilic groups useful with the linker of this invention include fatty acid derivatives that may or may not form micelles in aqueous medium and other specific lipophilic groups that modulate interactions between the carbohydrate rapamycin derivative and biological membranes.

The flexibility of the linker can be manipulated by the inclusion of ancillary groups that are bulky and/or rigid. The presence of bulky or rigid groups can hinder free rotation about bonds in the linker, or bonds between the linker and the ancillary group(s), or bonds between the linker and the functional groups. Rigid groups can include, for example, those groups whose conformational freedom is restrained by the presence of rings and/or bonds, for example, aryl, heteroaryl and heterocyclic groups. Other groups that can impart rigidity include polypeptide groups such as oligo- or polyproline chains.

Rigidity can also be imparted electrostatically. Thus, if the ancillary groups are either positively or negatively charged, the similarly charged ancillary groups will force the linker into a configuration affording the maximum distance between each of the like charges. The energetic cost of bringing the like-charged groups closer to each other, which is inversely related to the square of the distance between the groups, will tend to hold the linker in a configuration that maintains the separation between the like-charged ancillary groups. Further, ancillary groups bearing opposite charges will tend to be attracted to their oppositely charged counterparts and potentially may enter into both inter- and intramolecular ionic bonds. This non-covalent mechanism will tend to hold the linker in a conformation that allows bonding between the oppositely charged groups. The addition of ancillary groups which are charged, or alternatively, protected groups that bear a latent charge which is unmasked, following addition to the linker, by deprotection, a change in pH, oxidation, reduction or other mechanisms known to those skilled in the art, is within the scope of this invention.

Bulky groups can include, for example, large atoms, ions (e.g., iodine, sulfur, metal ions, etc.) or groups containing large atoms, polycyclic groups, including aromatic groups, non-aromatic groups, and structures incorporating one or more carbon-carbon bonds (i.e., alkenes and alkynes). Bulky groups can also include oligomers and polymers that are branched- or straight-chain species. Branched-species are expected to increase the rigidity of the structure more per unit molecular weight gain than are straight-chain species.

In view of the above, it is apparent that the appropriate selection of a linker group providing suitable orientation, entropy and physico-chemical properties is well within the skill of the art.

Linkers can be attached to rapamycin or a sugar by employing reactive functional groups. The reactive functional groups are selected relative to the functional groups available on rapamycin or the sugar for coupling, or which are introduced onto rapamycin or the sugar for this purpose. For example, reaction between a carboxylic acid of the linker and a primary or secondary amine of the sugar in the presence of suitable activating agents results in formation of an amide moiety covalently linking the sugar to the linker. Reaction between an amine group of the linker and a sulfonyl halide of the sugar results in formation of a sulfonamide moiety covalently linking the sugar to the linker. Reaction between an alkyl or aryl halide of the linker and an alcohol of the sugar results in formation of an ether moiety covalently linking the sugar to the linker.

Where functional groups are lacking, they can be created by suitable chemistries that are described in standard organic chemistry texts such as *Advanced Organic Chemistry*, Jerry March, John Wiley & Sons (5th Ed., 2000). The term linker embraces everything that is not considered to be part of the sugar or rapamycin. Linkers can be derived from linear compounds having reactive functional groups at the end of the linker.

Suitable divalent linkers include, by way of example, those derived from dicarboxylic acids, disulfonylhalides; dialdehydes, diketones, dihalides, diisocyanates, diamines, diols, mixtures of carboxylic acids, sulfonylhalides, aldehydes, ketones, halides, isocyanates, amines and diols. In each case, the carboxylic acid, sulfonylhalide, aldehyde, ketone, halide, isocyanate, amine and diol functional group is reacted with a complementary functionality on the sugar and rapamycin to form a covalent linkage. Such complementary functionality is well known in the art as illustrated in the above-discussed Table 1.

In embodiments of the invention, the linker (X) is selected from the group consisting of: (i) —$R^3C(O)$; (ii) —$C(O)R^3$, (iii) —$R^3S(O)_2$; or (iv) —$S(O)_2R^3$ where $R^3$ is selected from the group consisting of: (i) —$(CH_2)_p$— where p is an integer from 1 to 18, (ii) —$(CH_2)_n$—O—$(CH_2)_m$— where n and m are each independently an integer from 2 to 6, or (iii) a bond. It is to be understood that the linker (X) may be the same or different at each occurrence, i.e., at the 31 and 42 positions. In additional embodiments of the invention, the linker (X) is carbonyl (C═O), sulfonyl (O═S═O), or a single functional group. Carbonyl linkers may be in the 31 position, the 42 position, or both. In other embodiments, $R^1$ is —C(O)-Z and $R^2$ is H or $R^2$ is —C(O)-Z and $R^1$ is H.

Accordingly, rapamycin carbohydrate derivatives having the structure of formula I that are within the scope of this invention include, for example, those set forth below (including pharmaceutically acceptable salts thereof):

42-O-(Methyl-D-glucosylcarbonyl)rapamycin;
42-O-[2-(Methyl-D-glucosylcarbonyloxy)ethyl]rapamycin;
31-O-(Methyl-D-glucosylcarbonyl)rapamycin;
42-O-(2-Hydroxyethyl)-31-O-(methyl-D-glucosylcarbonyl)rapamycin;
42-O-(2-O-Methyl-D-fructosylcarbonyl)rapamycin;
42-O-[2-(2-O-Methyl-D-fructosylcarbonyloxy)ethyl]rapamycin;
42-O-(2-O-Methyl-L-fructosylcarbonyl)rapamycin;
42-O-[2-(2-O-Methyl-L-fructosylcarbonyloxy)ethyl]rapamycin;
31-O-(2-O-Methyl-D-fructosylcarbonyl)rapamycin;
42-O-(2-Hydroxyethyl)-31-O-(2-O-methyl-D-fructosylcarbonyl)rapamycin;
31-O-(2-O-Methyl-L-fructosylcarbonyl)rapamycin;
42-O-(2-Hydroxyethyl)-31-O-(2-O-methyl-L-fructosylcarbonyl)rapamycin;
42-O-(D-Allosylcarbonyl)rapamycin;
42-O-[2-(D-Allosylcarbonyloxy)ethyl]rapamycin;
42-O-(L-Allosylcarbonyl)rapamycin;
42-O-[2-(L-Allosylcarbonyloxy)ethyl]rapamycin;
31-O-(D-Allosylcarbonyl)rapamycin;
42-O-(2-Hydroxyethyl)-31-O-(D-allosylcarbonyl)rapamycin;
31-O-(L-Allosylcarbonyl)rapamycin;
42-O-(2-Hydroxyethyl)-31-O-(L-allosylcarbonyl)rapamycin;
42-O-(D-Fructoslylcarbonyl)rapamycin;
42-O-[2-(D-Fructoslylcarbonyloxy)ethyl]rapamycin;
42-O-(L-Fructoslylcarbonyl)rapamycin;
42-O-[2-(L-Fructoslylcarbonyloxy)ethyl]rapamycin;
31-O-(D-Fructoslylcarbonyl)rapamycin;
42-O-(2-Hydroxyethyl)-31-O-(D-fructoslylcarbonyl)rapamycin;

31-O-(L-Fructoslylcarbonyl)rapamycin;
42-O-(2-Hydroxyethyl)-31-O-(L-fructoslylcarbonyl)rapamycin;
42-O-(D-Fucitolylcarbonyl)rapamycin;
42-O-[2-(D-Fucitolylcarbonyloxy)ethyl]rapamycin;
42-O-(L-Fucitolylcarbonyl)rapamycin;
42-O-[2-(L-Fucitolylcarbonyloxy)ethyl]rapamycin;
31-O-(D-Fucitolylcarbonyl)rapamycin;
42-O-(2-Hydroxyethyl)-31-O-(D-fucitolylcarbonyl)rapamycin;
31-O-(L-Fucitolylcarbonyl)rapamycin;
42-O-(2-Hydroxyethyl)-31-O-(L-fucitolylcarbonyl)rapamycin;
42-O-(D-Glucalylcarbonyl)rapamycin;
42-O-[2-(D-Glucalylcarbonyloxy)ethyl]rapamycin;
42-O-(D-Glucosylcarbonyl)rapamycin;
42-O-[2-(D-Glucosylcarbonyloxy)ethyl]rapamycin;
42-O-(L-Glucosylcarbonyl)rapamycin;
42-O-[2-(L-Glucosylcarbonyloxy)ethyl]rapamycin;
31-O-(D-Glucalylcarbonyl)rapamycin;
42-O-(2-Hydroxyethyl)-31-O-(D-glucalylcarbonyl)rapamycin;
31-O-(D-Glucosylcarbonyl)rapamycin;
42-O-(2-Hydroxyethyl)-31-O-(D-glucosylcarbonyl)rapamycin;
31-O-(L-Glucosylcarbonyl)rapamycin;
42-O-(2-Hydroxyethyl)-31-O-(L-glucosylcarbonyl)rapamycin;
42-O-(D-Lactalylcarbonyl)rapamycin;
42-O-[2-(D-Lactalylcarbonyloxy)ethyl]rapamycin;
31-O-(D-Lactalylcarbonyl)rapamycin;
42-O-(2-Hydroxyethyl)-31-O-(D-lactalylcarbonyl)rapamycin;
42-O-(D-Sucrosylcarbonyl)rapamycin;
42-O-[2-(D-Sucrosylcarbonyloxy)ethyl]rapamycin;
31-O-(D-Sucrosylcarbonyl)rapamycin;
42-O-(2-Hydroxyethyl)-31-O-(D-sucrosylcarbonyl)rapamycin;
42-O-(D-Gentobiosylcarbonyl)rapamycin
42-O-[2-(D-Gentobiosylcarbonyloxy)ethyl]rapamycin;
31-O-(D-Gentobiosylcarbonyl)rapamycin
42-O-(2-Hydroxyethyl)-31-O-(D-gentobiosylcarbonyl)rapamycin
42-O-(D-Cellobiosylcarbonyl)rapamycin;
42-O-[2-(D-Cellobiosylcarbonyloxy)ethyl]rapamycin;
31-O-(D-Cellobiosylcarbonyl)rapamycin;
42-O-(2-Hydroxyethyl)-31-O-(D-cellobiosylcarbonyl)rapamycin;
42-O-(D-Turanosylcarbonyl)rapamycin;
42-O-[2-(D-Turanosylcarbonyloxy)ethyl]rapamycin;
31-O-(D-Turanosylcarbonyl)rapamycin;
42-O-(2-Hydroxyethyl)-31-O-(D-turanosylcarbonyl)rapamycin;
42-O-(D-Palatinosylcarbonyl)rapamycin;
42-O-[2-(D-Palatinosylcarbonyloxy)ethyl]rapamycin;
31-O-(D-Palatinosylcarbonyl)rapamycin;
42-O-(2-Hydroxyethyl)-31-O-(D-palatinosylcarbonyl)rapamycin;
42-O-(D-Isomaltosylcarbonyl)rapamycin;
42-O-[2-(D-Isomaltosylcarbonyloxy)ethyl]rapamycin;
31-O-(D-Isomaltosylcarbonyl)rapamycin;
42-O-(2-Hydroxyethyl)-31-O-(D-isomaltosylcarbonyl)rapamycin;
42-O-(D-Maltulosylcarbonyl)rapamycin;
42-O-[2-(D-Maltulosylcarbonyloxy)ethyl]rapamycin;
42-O-(D-Maltosylcarbonyl)rapamycin;
42-O-[2-(D-Maltosylcarbonyloxy)ethyl]rapamycin;
31-O-(D-Maltulosylcarbonyl)rapamycin;
42-O-(2-Hydroxyethyl)-31-O-(D-maltulosylcarbonyl)rapamycin;
31-O-(D-Maltosylcarbonyl)rapamycin;
42-O-(2-Hydroxyethyl)-31-O-(D-maltosylcarbonyl)rapamycin;
42-O-(L-Sorbosylcarbonyl)rapamycin;
42-O-(D-Sorbosylcarbonyl)rapamycin;
31-O-(L-Sorbosylcarbonyl)rapamycin;
31-O-(D-Sorbosylcarbonyl)rapamycin;
42-O-[2-(L-Sorbosylcarbonyloxy)ethyl]rapamycin;
42-O-[2-(D-Sorbosylcarbonyloxy)ethyl]rapamycin;
42-O-(2-Hydroxyethyl)-31-O-(D-sorbosylcarbonyl)rapamycin;
42-O-(2-Hydroxyethyl)-31-O-(L-sorbosylcarbonyl)rapamycin;
42-O-(D-Lactosylcarbonyl)rapamycin;
42-O-[2-(D-Lactosylcarbonyloxy)ethyl]rapamycin;
31-O-(Methyl-D-lactosylcarbonyl)rapamycin;
42-O-(2-Hydroxyethyl)-31-O-(methyl-D-lactosylcarbonyl)rapamycin;
42-O-(D-Melibiosylcarbonyl)rapamycin;
31-O-(D-Melibiosylcarbonyl)rapamycin;
42-O-(2-Hydroxyethyl)-31-O-(D-melibiosylcarbonyl)rapamycin;
42-O-(D-Leucrosylcarbonyl)rapamycin;
42-O-[2-(D-Leucrosylcarbonyloxy)ethyl]rapamycin;
31-O-(D-Leucrosylcarbonyl)rapamycin;
42-O-(2-Hydroxyethyl)-31-O-(D-leucrosylcarbonyl)rapamycin;
42-O-(D-Rafinosylcarbonyl)rapamycin;
42-O-[2-(D-Rafinosylcarbonyloxy)ethyl]rapamycin;
31-O-(D-Rafinosylcarbonyl)rapamycin;
42-O-(2-Hydroxyethyl)-31-O-(D-rafinosylcarbonyl)rapamycin;
42-O-(D-Isomaltotriosylcarbonyl)rapamycin;
42-O-[2-(D-Isomaltosylcarbonyloxy)ethyl]rapamycin;
31-O-(D-Isomaltotriosylcarbonyl)rapamycin;
42-O-(2-Hydroxyethyl)-31-O-(D-isomaltotriosylcarbonyl)rapamycin;
42-O-(D-Cellotetraosylcarbonyl)rapamycin;
42-O-[2-(D-Cellotetraosylcarbonyloxy)ethyl]rapamycin;
31-O-(D-Cellotetraosylcarbonyl)rapamycin;
42-O-(2-Hydroxyethyl)-31-O-(D-cellotetraosylcarbonyl)rapamycin;
42-O-(Valiolylcarbonyl)rapamycin
42-O-[2-(D-Valiolylcarbonyloxy)ethyl]rapamycin;
31-O-(Valiolylcarbonyl)rapamycin
42-O-(2-Hydroxyethyl)-31-O-(valiolylcarbonyl)rapamycin
42-O-(Valiolonylcarbonyl)rapamycin
42-O-[2-(D-Valiolonylcarbonyloxy)ethyl]rapamycin;
31-O-(Valiolonylcarbonyl)rapamycin
42-O-(2-Hydroxyethyl)-31-O-(valiolonylcarbonyl)rapamycin
42-O-(Valienolylcarbonyl)rapamycin
42-O-[2-(D-Valienolylcarbonyloxy)ethyl]rapamycin;
31-O-(Valienolylcarbonyl)rapamycin
42-O-(2-Hydroxyethyl)-31-O-(valienolylcarbonyl)rapamycin
42-O-(Valienoneylcarbonyl)rapamycin
42-O-[2-(D-Valienoneylcarbonyloxy)ethyl]rapamycin;
31-O-(Valienoneylcarbonyl)rapamycin
42-O-(2-Hydroxyethyl)-31-O-(valienoneylcarbonyl)rapamycin In addition, the invention is directed to a rapamycin derivative having the structure of formula I wherein n=1, $R^1$ is H and R² is X—Z, wherein X is a linker, and Z is a carbohydrate moiety independently selected from the group consisting of a monosaccharide, an oligosaccharide and a pseudosugar.

The invention is also directed to a pharmaceutical composition comprising the aforementioned rapamycin carbohydrate derivative, or a pharmaceutically acceptable salt thereof, and a pharmaceutically acceptable carrier.

Preparation of the Rapamycin Carbohydrate Derivatives

A general procedure for synthesizing rapamycin carbohydrate derivatives of the present invention involves the coupling of a monosaccharide, oligosaccharide, pseudosugar or sugar derivative to the 31- and/or 42-positions of activated rapamycin.

Figure 2:
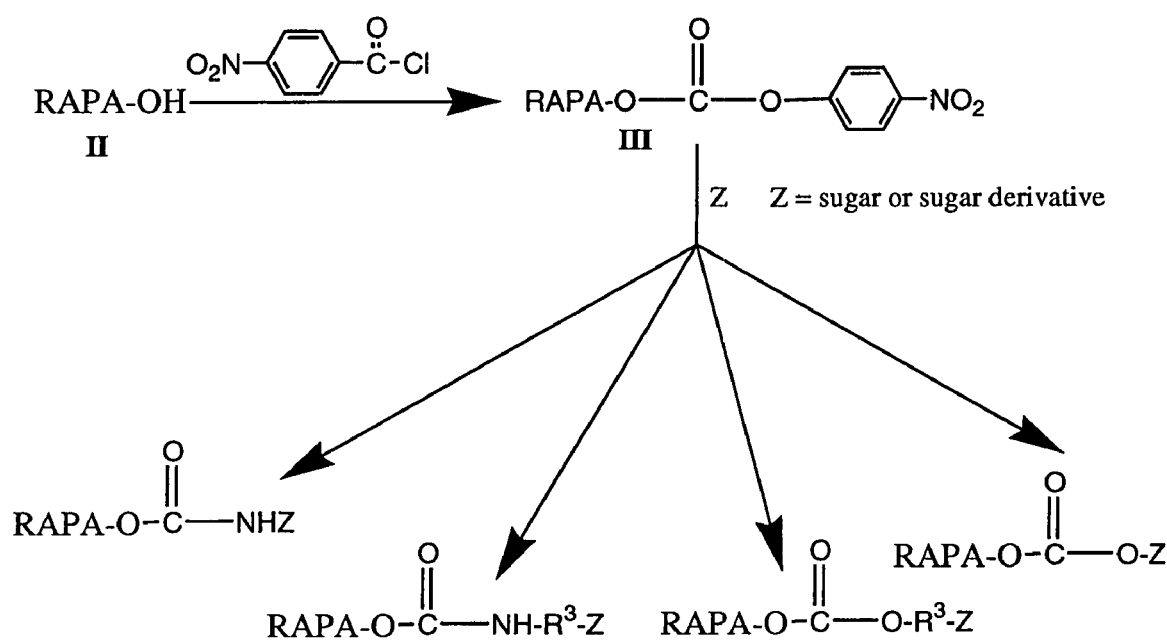
FIG. 2 depicts a general approach to the preparation of rapamycin carbohydrate derivatives of the present invention. "RAPA-OH" stands for rapamycin, wherein the hydroxyl group (—OH) may be any of the hydroxyl groups of rapamycin.

For example, as depicted in FIG. 2, rapamycin (II) can be reacted with p-nitrophenyl chloroformate to yield an activated rapamycin (III). Under carefully controlled conditions, the reaction will preferentially take place at the 42-hydroxyl position. By altering the reaction conditions, both the 31- and 42-hydroxyl groups can be similarly activated. Selective activation of the 31-hydroxyl group can be accomplished by.first protecting the 42-hydroxyl moiety with, for example an alkylsilyl group such as triethylsilyl, triisopropylsilyl or tert-butyldimethylsilyl, and then reacting with p-nitrophenyl chloroformate or other chloroformates. Removal of the protecting group then affords rapamycin activated at the 31-hydroxyl position. Thus, it is possible to prepare a rapamycin derivative that is selectively activated at the 31-position, the 42-position, or both.

Thereafter, in the second step, a sugar moiety or sugar derivative is reacted with an activated rapamycin (III) to give a rapamycin carbohydrate derivative. When the reactive functional group on the sugar moiety or sugar derivative is a hydroxyl group, the reaction with activated rapamycin may take place on a primary hydroxyl group to form a carbonate linkage to rapamycin. The resulting linker is a carbonyl group. When the reactive functional group on the sugar or sugar derivative is an amino group (which can be situated at any position of the sugar), a carbamate linkage to rapamycin results and the resulting linker is a carbonyl group. Amino substituted sugar derivatives, e.g., sugar-X—NH₂ or sugar-NH₂, can be prepared from precursors by conventional methods. For example, reduction of sugar-X—N₃ or de-phthaloylation of sugar-X-NPhth, where Phth is phthalyl, yields the amino substituted sugar derivative. These precursors can be synthesized by glycosidation of linker moieties with appropriately activated glycosyl donors.

Thus, using the general approach described herein is it possible to prepare a wide range of rapamycin carbohydrate derivatives in which the 31- and/or 42-hydroxyl groups are modified with a wide range of sugars or sugar derivatives.

It is contemplated that hydroxyl groups of rapamycin or a rapamycin metabolite, including those that are located in positions other than 31- and 42-, can also be glycosylated as described herein, and the resultant rapamycin carbohydrate derivatives will also exhibit higher water-solubility and/or enhanced pharmacokinetic and/or pharmacodynamic properties compared to their unglycosylated counterparts.

Rapamycin metabolites are known in the art. For example, Streit et. al. structurally identified several rapamycin metabolites from human liver microsomes. See, F. Streit et al., Drug Metabol. Disp., 24, 1272 (1996). These include 41-demethyl rapamycin, 7-demethyl rapamycin, 11-hydroxy rapamycin, and a 24-hydroxy ester hydrolysis degradation product of rapamycin. It has also beeri shown that the metabolites of rapamycin can undergo this ester hydrolysis. Streit also partially identified di, tri, and tetra hydroxylated rapamycin metabolites. Wang et. al. found 16 hydroxylated and/or demethylated metabolites in the bile of rapamycin treated rats. See, C. K. Wang et al., Proceedings of the 41$^{st}$ ASMS Conference on Mass Spectrometry and Allied Topics, San Francisco, 545 (1993). Nickmilder et. al. identified a 3,4 and 5,6 dihydrodiol rapamycin metabolite in rat liver microsomes. See, M. J. M. Nickmilder et al., Xenobiotica, 27, 869 (1997). In trough whole blood, Streit et. al. have identified 41-demethyl, hydroxy, dihydroxy, and didemethyl rapamycin metabolites. See, F. Streit et al., Clin. Chem., 42, 1417 (1996). These metabolites accounted for 56% of total rapamycin derivatives measured. Finally, Leung et. al. looked at the disposition of [$^{14}$C]-rapamycin in healthy male volunteers. They found that rapamycin represented approximately 35% of the total radioactivity in blood and that 41-demethyl, 7-demethyl, and several hydroxy, hydroxydemethyl, and didemethyl rapamycin metabolites individually represented between 1 and 12% of the total radioactivity. Rapamycin metabolites can be isolated from a number of various sources, including but not limited to blood, urine or feces samples, from liver microsomes or from microorganism cultures.

Accordingly, in addition to 31- and 42-, the hydroxyl groups of particular interest include those at the 27-, 41-, 3-, 4-, 5-, 6-, 7-, 11- and 24-positions of rapamycin and rapamycin metabolites.

Pharmaceutical Compositions and Utility

The compounds of this invention may be administered neat or with a pharmaceutical carrier to an animal, such as a warm blooded mammal, and especially humans, in need thereof. The pharmaceutical compositions may also contain other drugs, particularly drugs known to have different mechanisms of action. Thus, the pharmaceutical compositions may contain, in addition to the compounds of the present invention, at least one drug of another class, for example, a calcineurin inhibitor, a steroid or other immunomodulatory compounds which may interfere with DNA synthesis or intra- or inter-cellular signaling or other cell processes: Examples of calcineurin inhibitors include Cyclosporin A (available from Novartis as Sandimmune® and Neoral® and FK506 (also known as tacrolimus or Prograf® available from Fujisawa). Examples of cyclosporine derivatives are those disclosed in WO99/18120. Examples of steroids include predisone, prednisolone or methylprednisolone. Examples of these immunomodulatory compounds include azothioprine, mycophenolic acid (mycophenolate mofitil or Cellcept® available from Roche), leflunomide available from Aventis, Brequinar, Mizoribine, antibodies including α-LFA-1, and α-ICAM-1, thimoglobuline, IL2R antagonists including basiliximab (Stimulect®), and daclizumab (Zenapax®), alemtuzumab (Campath 1H®, a humanized monoclonal antibody recognizing CD52), Orthoclone OKT3® or muromonab CD3, Atgam(R) lymphocyte immune globulin, ATG (antithymocyte globulin), and other compounds. The individual drugs, and the rapamycin carbohydrate derivative, may be formulated separately as distinct components of the pharmaceutical composition, and administered together or separately.

The pharmaceutically effective carrier may be solid or liquid. A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets may contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs, and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, surfactants, buffers, preservatives, sweeteners, flavoring agents, suspending agents, thickening agents, colors, viscosity regulators, stabilizers or osmo-regujators. Suitable examples of liquid carriers for oral and parenteral administration include water (partially containing additives as above, e.g. cellulose derivatives, possibly sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions that are sterile solutions or suspensions are suitable for intramuscular, intraperitoneal, and subcutaneous injection. Sterile solutions can also be administered intravenously. The compound can also be administered orally either in liquid or solid composition form. Pulmonary administration is also contemplated.

The pharmaceutical composition can be in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The dosage to be used in the treatment must be subjectively determined by the attending physician.

In addition, the compounds of this invention may be employed as a solution, cream, or lotion by formulation with pharmaceutically acceptable vehicles administered to an affected area.

The compounds of this invention can also be used in conjunction with a medical device. For example, a rapamycin carbohydrate derivative as a component of a drug-coated or impregnated intravascular stent may be used to inhibit neointimal tissue proliferation and thereby prevent restenosis (See, for example U.S. Pat. No. 5,665,728). Rapamycin carbohydrate derivatives can also be used as a component of other drug-coated or impregnated medical devices such as catheters, pumps, ordrug-delivery medical devices such as beads or discs containing drugs. The presence of rapamycin, a potent immunosuppressant, may decrease inflammation, rejection, or other immune responses to the presence of these implantable medical devices in the body.

The following examples are offered to illustrate this invention and are not to be construed in any way as limiting the scope of the present invention.

EXAMPLES

In the examples below, the following abbreviations have the following meanings. If an abbreviation is not defined, it has its generally accepted meaning.

| | |
|---|---|
| g = | gram |
| mg = | milligram |
| kg = | kilogram |
| mmol = | millimole |
| M = | molar |
| N = | Normal |
| mL = | milliliter |
| min = | minute |
| BzCl = | benzoyl chloride |
| DMAP = | 4-dimethylaminopyridine |
| DMS = | dimethyl sulfate |
| Py = | Pyridine |
| DMF = | N,N-dimethylformamide |
| Me = | methyl |
| HOAt = | 1-hydroxy-7-azabenzotriazole |
| HOBT = | 1-hydroxybenzotriazole hydrate |
| TBDMSiCl = | tert-butyldimethylsilyl chloride |
| AcOH = | acetic acid |
| THF = | tetrahydrofuran |
| LC/MS or = LCMS | liquid chromatography/mass spectroscopy |
| HPLC = | high performance liquid chromatography |
| conc. = | concentrated |
| eq. = | equivalents |

In the following examples and procedures, the starting materials are available commercially from Aldrich Chemical Company, Inc., Milwaukee, Wis. 53233 USA; Lancaster Synthesis, Inc., N.H. 03087 USA; Sigma, St. Louis Mo. 63178 USA; Maybridge Chemical Co. Trevillett, Tintagel, Cornwall PL34 OHW United Kingdom; TCI America, Portland Oreg. 97203; Frontier Scientific, Utah, USA; and Bachem, Torrance, Calif., USA.

Example 1

Synthesis of 42-O-(D-Fructosylcarbonyl)rapamycin

FIG. 3 depicts the method of synthesis for 42-O-(D-Fructosylcarbonyl)rapamycin. The detailed procedure is described below:

42-O-(4-nitrophenyloxycarbonyl)rapamycin

A solution of 10.0 g of rapamycin in 50 mL of dichloromethane and 10 mL of dry pyridine was cooled to −78° C. under a nitrogen atmosphere. To this solution 3.31 g of 4-nitrophenyl chloroformate was added and the reaction mixture was stirred for 1 hour at −78° C., and then brought directly to room temperature. Reaction was complete after 2 hours. The mixture was diluted with water and extracted with dichloromethane. The organic phase was washed with water, dried over $Na_2SO_4$ and evaporated. Chromatography on a silica gel column (solvent:hexanes-ethyl acetate, 2:1) gave 9.66 g of 42-O-(4-nitrophenyloxycarbonyl)rapamycin as a yellowish solid (freeze dried from benzene). $C_{58}H_{82}N_2O_{17}$, M=1078.6; MS(ES+): m/z=1101.7 (M+Na)$^+$.

42-O-(D-Fructosylcarbonyl)rapamycin

To a solution of D-fructose (2.025 g, 11.24 mmol) and DMAP (250 mg) in N,N-dimethylformamide (25 mL) 42-O-(4-nitrophenyloxycarbonyl)rapamycin (4.05 g, 3.757 mmol) was added and the reaction mixture was stirred at room temperature for 24 hours. The solvent was evaporated under high vacuum and the residue was flash chromatographed on a silica gel column using dichloromethane-methanol (9:1) as eluent. Obtained product was re-purified on a preparative HPLC column (80% methanol-20% water, flow 10 mL/min.), yielding 1.461 g of 42-O-(D-fructosylcarbonyl)rapamycin as white solid (freeze dried from benzene). $C_{58}H_{89}NO_{20}$, M=1119.6; MS(ES+): m/z=1142.7 $(M+Na)^+$ In the alternative HOBT (or HOAT) may be employed in place of DMAP as disclosed in example 3.

Example 2

Following procedures analogous to that outlined in Example 1, and employing the appropriate sugars or sugar derivatives, the following compounds have been obtained:
42-O-(D-Glucosylcarbonyl)rapamycin
42-O-(Methyl-D-glucosylcarbonyl)rapamycin
42-O-(D-Allosylcarbonyl)rapamycin
42-O-(D-Fructosylcarbonyl)rapamycin
42-O-(L-Fructosylcarbonyl)rapamycin
42-O-(D-Fucitolylcarbonyl)rapamycin
42-O-(L-Fucitolylcarbonyl)rapamycin
42-O-(D-Glucalylcarbonyl)rapamycin
42-O-(L-Sorbosylcarbonyl)rapamycin
42-O-(2-O-Methyl-D-fructosylcarbonyl)rapamycin
42-O-(D-Lactalylcarbonyl)rapamycin
42-O-(D-Sucrosylcarbonyl)rapamycin
42-O-(D-Gentobiosylcarbonyl)rapamycin
42-O-(D-Cellobiosylcarbonyl)rapamycin
42-O-(D-Turanosylcarbonyl)rapamycin
42-O-(D-Palatinosylcarbonyl)rapamycin
42-O-(D-Isomaltosylcarbonyl)rapamycin
42-O-(D-Maltulosylcarbonyl)rapamycin
42-O-(D-Maltosylcarbonyl)rapamycin
42-O-(D-Lactosylcarbonyl)rapamycin
42-O-(Methyl-D-lactosylcarbonyl)rapamycin
42-O-(D-Melibiosylcarbonyl)rapamycin
42-O-(D-Leucrosylcarbonyl)rapamycin
42-O-(D-Rafinosylcarbonyl)rapamycin
42-O-(D-Isomaltotriosylcarbonyl)rapamycin
42-O-(D-Cellotetraosylcarbonyl)rapamycin

Example 3

Synthesis of 31-O-(D-Fructosylcarbonyl)rapamycin

Figure 4:
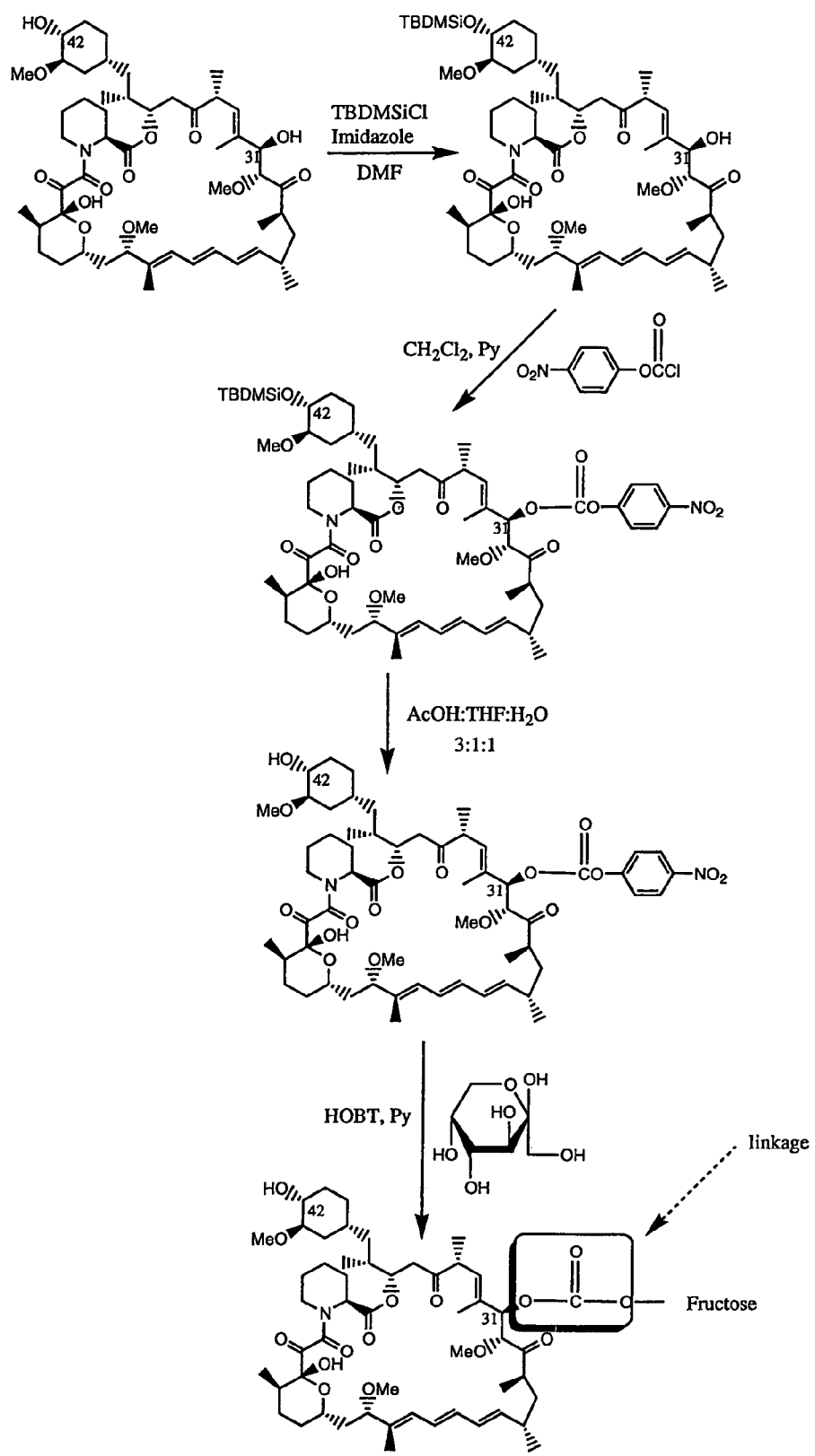
FIG. 4 depicts the reaction pathway for the synthesis of 31-O-(D-fructosylcarbonyl)rapamycin.

FIG. 4 depicts the method of synthesis for 31-O-(D-Fructosylcarbonyl)rapamycin. The detailed procedure is described below:

42-O-(tert-Butyldimethylsilyl)rapamycin

To a solution of rapamycin (10 g) and imidazole (2.2 g) in N,N-dimethylformamide (40 mL) tert-butyldimethylsilyl chloride (1.76 g) was added, and the reaction mixture was stirred at room temperature under nitrogen for 5 days. The solvent was evaporated under high vacuum and the residue was chromatographed on a silica gel column (solvent: hexanes-ethyl acetate, 3:2) yielding 5.84 g of 42-O-(tert-butyldimethylsilyl)rapamycin as off-white foam. $C_{57}H_{93}NO_{13}Si$, M=1027.6; MS(ES+): m/z=1050.7 $(M+Na)^+$.

42-O-(tert-Butyldimethylsilyl)-31-O-(4-nitrophenyloxycarbonyl)rapamycin

42-O-(tert-Butyldimethylsilyl)rapamycin (5.84 g) was dissolved in dichloromethane (30 mL) and pyridine (6 mL), 4-nitrophenyl chloroformate (2.582 g) was added and the reaction mixture was stirred under nitrogen at room temperature for 2 hours. Solvents were evaporated and the residue purified on a silica gel column. Elution with hexanes-ethyl acetate (3:1) gave title compound as yellowish foam (5.4 g). $C_{64}H_{96}N_2O_{17}Si$, M=1192.6; MS(ES+): m/z=1215.6 $(M+Na)^+$.

31-O-(4-nitrophenyloxycarbonyl)rapamycin

42-O-(tert-Butyldimethylsilyl)-31-O-(4-nitrophenyloxycarbonyl)rapamycin (5.4 g) was dissolved in a mixture of acetic acid (30 mL), tetrahydrofuran (10 mL) and water (10 mL). It was stirred at room temperature for 20 hours. The reaction mixture was diluted with water and extracted with ethyl acetate (3×200 mL). The organic phase was dried over anhydrous sodium sulfate, filtered and evaporated. Silica gel column chromatography (solvent:hexanes-ethyl acetate, 3:2) gave 2.1 g of 31-O-(4-nitrophenyloxycarbonyl)rapamycin as yellowish solid (freeze dried from benzene). $C_{58}H_{82}N_2O_{17}$, M=1078.6; MS(ES+): m/z=1101.6 $(M+Na)^+$.

31-O-(D-Fructosylcarbonyl)rapamycin

A mixture of 31-O-(4-nitrophenyloxycarbonyl)rapamycin (1.3 g), D-fructose (0.434 g), and 1-hydroxybenzotriazole (HOBT) (0.325 g) in dry pyridine (20 mL) was stirred at room temperature for 3 days. Then, the solvent was evaporated under reduced pressure and the residue was chromatographed on a silica gel column. Elution with dichloromethane-methanol (10:1) provided 31-O-(D-fructosylcarbonyl)rapamycin (0.625 g, 46%) as white solid (freeze dried from benzene). $C_{58}H_{89}NO_{20}$, M=1119.6; MS(ES+): m/z=1142.7 $(M+Na)^+$.

In an analogous manner, 31-O-(D-allosylcarbonyl)rapamycin was also prepared. In addition, in the alternative, DMAP may be employed in place of HOBT as disclosed in example 1.

Example 4

Synthesis of 42-O-(2-O-methyl-β-D-fructosylcarbonyl)rapamycin

1,3,4,5-Tetra-O-benzoyl-β-D-fructopyranose

A mixture of anhydrous pyridine (52 mL), benzoyl chloride (51.5 mL, 0.444 mmol) and anhydrous dichloromethane (125 mL) was cooled to −10° C. Finely powdered fructose (20 g, 0.111 mmol) was added portion wise and the reaction mixture was stirred at −10° C. for 18 hours. The reaction mixture was quenched with ice water, diluted with dichloromethane and transferred to separatory funnel. Organic layer was separated and washed with 5% citric acid, saturated sodium bicarbonate, water, and dried over sodium sulfate. It was filtered and the solvent evaporated. The residue was dissolved in diethyl ether (75 ml) then added slowly to hexanes (300 ml) to give a white solid which upon drying afforded 58.9 g (89%) of 1,3,4,5-tetra-O-benzoyl-β-D-fructopyranose 1,3,4,5-Tetra-O-benzoyl-2-O-methyl-β-D-fructopyranose To a solution of 1,3,4,5-tetra-O-benzoyl-β-D-fructopyranose (10.00 g, 16.8 mmol) in acetone (40 mL) dimethyl sulfate (2.4 ml, 25.16 mmoles, 1.5 eq.) was added followed by potassium carbonate (3.48 g, 25.16 mmoles) and the reaction mixture was stirred at 50° C. under nitrogen for 18 hours. Solvents were removed under vacuo and the resulting residue was dissolved in ethyl acetate (150 ml), washed with 5% citric acid, water, brine, dried over sodium sulfate, filtered and concentrated to an oily solid. Purification on a silica gel column (hexane:ethyl acetate, 4:1) afforded 10.0 g (98%) of title compound as white foam.

2-O-methyl-β-D-fructopyranose

A solution of sodium methoxide (0.5 M in methanol, 10.0 ml) was added to a vigorously stirred solution of 1,3,4,5-tetra-O-benzoyl-2-O-methyl-β-D-fructopyranose (10.0 g, 16.4 mmol) in anhydrous methanol. After stirring for 1.5 hrs at room temperature the reaction was complete. The pH was adjusted to 7.0 with Amberlite IRC-50 (~4.0 g). The solids were removed by filtration and the filtrate was concentrated in vacuo. Purification on a silica gel column (methanol:dichloromethane, 4:1 and 3:1) provided the product as white foam 2.70 g (81%).

42-O-(2-O-methyl-β-D-fructosylcarbonyl)rapamycin

A mixture of 42-O-(4-nitrophenyloxycarbonyl)rapamycin (10.0 g, 9.3 mmol), 2-O-methyl-β-D-fructopyranose (6.2 g, 28 mmol, 3 eq.), and 1-hydroxy-7-azabenzotriazole (HOAt) (2.5 g, 2 eq.) in dry pyridine (60 mL) was stirred at room temperature for 4 days. Then, the solvent was evaporated under reduced pressure and the residue was re-dissolved in ethyl acetate, washed with water. Organic layer was evaporated and the residue chromatographed on a silica gel column. Elution with dichloromethane-methanol (100:5) gave 42-O-(2-O-methyl-β-D-fructosylcarbonyl)rapamycin (4.7 g,) as white solid (freeze dried from benzene). $C_{59}H_{91}NO_{20}$, M=1133.7; MS (ES+): m/z=1156.7 (M+Na)$^+$.

Example 5

Stability of Rapamycin Carbohydrate Derivatives Toward Hydrolysis in Acidic Media The stability toward hydrolysis of various rapamycin carbohydrate derivatives in acidic media was investigated by dissolving the compounds in 70/30 methanol/0.1N HCl (pH 1.5) and then measuring by HPLC the amount of free rapamycin in the samples at 1 hour to determine the extent of hydrolysis. The results are summarized in Table 2.

TABLE 2

ACID CATALYZED HYDROLYSIS OF RAPAMYCIN CARBOHYDRATE DERIVATIVES

| Compound | Extent of Hydrolysis (%) |
| --- | --- |
| 42-O-(D-Fructosylcarbonyl)rapamycin | <1 |
| 42-O-(D-Glucosylcarbonyl)rapamycin | <1 |
| 42-O-(D-Maltulosylcarbonyl)rapamycin | <5 |
| 42-O-(L-Fucitolylcarbonyl)rapamycin | <1 |
| 42-O-(D-Lactalylcarbonyl)rapamycin | <1 |

TABLE 2-continued

ACID CATALYZED HYDROLYSIS OF RAPAMYCIN CARBOHYDRATE DERIVATIVES

| Compound | Extent of Hydrolysis (%) |
| --- | --- |
| 31-O-(D-Fructosylcarbonyl)rapamycin | <1 |
| 42-O-(D-Allosylcarbonyl)rapamycin | <1 |

As can be seen in Table 2, all compounds exhibited good stability in acidic media with little or no observable hydrolysis.

Example 6

Hydrolysis of Rapamycin Carbohydrate Derivatives in Human Whole Blood

The ability of various rapamycin carbohydrate derivatives to release free rapamycin via hydrolysis in whole blood was investigated by spiking the compounds in human whole blood and then measuring by HPLC the amount of free rapamycin in the samples at 1 hour to determine the extent of hydrolysis. The results are summarized in Table 3.

TABLE 3

HYDROLYSIS OF RAPAMYCIN CARBOHYDRATE DERIVATIVES IN WHOLE BLOOD

| Compound | Extent of Hydrolysis (%) |
| --- | --- |
| 42-O-(D-Fructosylcarbonyl)rapamycin | 28 ± 2 |
| 42-O-(D-Glucosylcarbonyl)rapamycin | 5 ± 1 |
| 42-O-(D-Maltulosylcarbonyl)rapamycin | 13 ± 4 |
| 42-O-(L-Fucitolylcarbonyl)rapamycin | 31 ± 4 |
| 42-O-(D-Lactalylcarbonyl)rapamycin | 2 ± 1 |
| 31-O-(D-Fructosylcarbonyl)rapamycin | 23 ± 0.5 |
| 42-O-(D-Allosylcarbonyl)rapamycin | 39 ± 4 |
| 31-O-(D-Allosylcarbonyl)rapamycin | 34 ± 2 |

As shown in Table 3, the extent of hydrolysis in human whole blood varied greatly depending on the nature of the carbohydrate moiety. The incorporation via carbonate linkages of sugars such as D-fructose, L-fucitol or D-allose generally led to a higher degree of hydrolysis than was observed when D-glucose, D-maltulose, and D-lactal were employed. The results also show that when a suitable sugar is chosen, both 31-O- and 42-O-rapamycin carbohydrate derivatives are effective at releasing free rapamycin in whole blood. Additionally, previous, similar experiments that investigated the hydrolysis in whole blood of rapamycin carbohydrate derivatives with carbamate linkages showed little or no hydrolysis in contrast to many of the compounds with carbonate linkages in Table 3.

Example 7

Comparison of the In Vitro Immunosuppressive Activity of Rapamycin Carbohydrate Derivatives with Carbonate and Carbamate Linkages The immunosuppressive activity of rapamycin, 42-O-(D-Fructosylcarbonyl)rapamycin and a carbamate-linked analog of 42-O-(D-Fructosylcarbonyl)rapamycin (a non-hydrolyzable form of 42-O-(D-Fructosylcarbonyl)rapamycin) was assessed in primary blood lymphocyte cultures (PBMC) using alamar blue as detection of cell proliferation. The carbamate analog of 42-O-(D-Fructosylcarbonyl)rapamycin is formed from an amino sugar wherein the carbohydrate moiety is attached to the carbonyl linker through the amino nitrogen atom of the amino sugar, thereby forming a carbamate linkage. FIG. 5 illustrates that 42-O-(D-Fructosylcarbonyl)rapamycin shows cell proliferation inhibition equivalent to rapamycin, while the non-hydrolyzable carbamate-linked analog does not possess any intrinsic immunosuppressive activity. This data indicates that the active species is rapamycin resulting from the hydrolysis of 42-O-(D-Fructosylcarbonyl)rapamycin over the course of the 3-day culturing, and not non-hydrolysed 42-O-(D-Fructosylcarbonyl)rapamycin. In other words, the prodrug does not appear to possess any intrinsic immunosuppressive activity and must be hydrolyzed to rapamycin in order to exhibit the desired pharmacological effect. This experiment also demonstrates the importance of the selection of the linkage between the carbohydrate moiety and rapamycin as, in this example, a carbonate linkage allows for the desired hydrolysis to occur whereas the carbamate linkage remains intact and little or no rapamycin is released.

Example 8

Comparison of Pharmacokinetic Profiles of Rapamycin and Rapamycin Carbohydrate Derivatives in Rats The pharmacokinetic profiles in rats of selected rapamycin carbohydrate derivatives were determined to investigate the ability of the derivatives to deliver free rapamycin into the bloodstream in vivo. Briefly, Sprague Dawley rats were orally dosed with rapamycin and derivatives at 2.5 or 10 mg/kg. Whole blood was extracted via jugular bleed over 24 hours and frozen at −20° C. until analysis. Whole blood was analyzed by Liquid Chromatography Mass Spectrometry for the presence of rapamycin. The results are summarized in FIGS. 6, 7 and 8.

As can be seen in FIGS. 6 and 7, upon oral administration of rapamycin a rapid rise in rapamycin concentration in the blood was observed with a maximum concentration reached at approximately 30 minutes. The level of rapamycin then dropped quite rapidly over the next several hours. A similar profile was observed for 42-O-(D-glucosylcarbonyl)rapamycin. Surprisingly, however, when 42-O-(D-fructosylcarbonyl)rapamycin or 42-O-(L-fucitolylcarbonyl)rapamycin were administered orally the level of rapamycin in the blood rose gradually to reach a maximum concentration at approximately 3 hours before gradually decreasing over time (FIG. 6). A similar profile was observed for both 31-O-(D-fructosylcarbonyl)rapamycin and 31-O-(D-allosylcarbonyl)rapamycin (FIG. 7) as well as 42-O-(D-allosylcarbonyl)rapamycin, 42-O-(D-sorbosylcarbonyl)rapamycin and 42-O-(2-O-methyl-D-fructosylcarbonyl)rapamycin (FIG. 8). The delayed kinetics observed for selected compounds may offer the advantage of allowing for less frequent dosing than that typical for rapamycin. Additionally, the gradual rise in rapamycin concentration associated with selected rapamycin carbohydrate derivatives may ameliorate toxic effects associated with the rapid rise in drug concentration when rapamycin itself is orally administered.

A second observation from FIGS. 6, 7 and 8 is that the variability in the concentration of rapamycin, as demonstrated by the standard deviations shown on the graphs, was considerably lower for the rapamycin carbohydrate derivatives than for rapamycin itself. Thus, the compounds of the present invention may also have the advantage of reduced inter-individual variability that could allow for more consistent, predictable dosing.

These experiments demonstrated that careful selection of the glycosyl substituent has a profound impact on the pharmacokinetic profiles of the rapamycin carbohydrate derivatives and that the compounds of the present invention may possess considerable advantage, including pharmacokinetic advantages, over rapamycin itself.

Example 9

Comparison of GI Tract Toxicity of Rapamycin and 42-O-(D-Fructosylcarbonyl)rapamycin in a Canine Model Beagle dogs are considered to be a hypersensitive model of gastrointestinal tract toxicity associated with rapamycin. See, S. N. Sehgal et al., Medicinal Research Reviews 14, 1 (1994). Even short exposures of low dose rapamycin given orally to dogs is known to result in rapid weight loss due to ulceration occurring from the mouth to the colon secondary to necrotizing fibrinoid vasculitis. As summarized in Table 4, when 2 beagle dogs were given a single oral dose of rapamycin at 10 mg/kg both dogs became lethargic and lost over 30% of their body weight in less than 1 week resulting from reduced food intake. The animals did not recover. Another beagle dog given the same dose of 42-O-(D-fructosylcarbonyl)rapamycin showed no overt physical changes and maintained a normal food intake. All three dogs had similar blood levels of rapamycin as measured by LCMS. In a fourth dog a dose of 1 mg/kg 42-O-(D-fructosylcarbonyl)rapamycin resulted in slight lethargy but the dog quickly recovered. A subsequent dose of rapamycin (1 mg/kg) one week later resulted in severe lethargy and weight loss, from which the animal did not recover.

TABLE 4

GASTROINTESTINAL TOLERABILITY IN BEAGLE DOGS

| Dog # | Drug Treatment | Dose (mg/kg) | Observations |
| --- | --- | --- | --- |
| 1 | Rapamycin | 10 | Lethargic 30% weight loss No recovery |
| 2 | Rapamycin | 10 | Lethargic 30% weight loss No recovery |
| 3 | 42-O-(D-Fructosylcarbonyl) rapamycin | 10 | Normal |
| 4 | 42-O-(D-Fructosylcarbonyl) rapamycin | 1 | Lethargic Recovered |
| 4 | Rapamycin | 1 | 30% weight loss No recovery |

This experiment clearly demonstrates that oral administration of 42-O-(D-fructosylcarbonyl)rapamycin resulted in little or no overt sign of gastrointestinal toxicity in a hypersensitive dog model as compared to rapamycin which led to signs of severe toxicity. This result further demonstrates the potential of the rapamycin carbohydrate derivatives of the present invention to improve the pharmacodynamic profile of rapamycin.

Example 10

Comparison of Serum Cholesterol Levels in Rats Treated with Rapamycin and 42-O-(D-Fructosylcarbonyl)rapamycin 42-O-(D-fructosylcarbonyl)rapamycin and rapamycin were tested head-to-head in Sprague-Dawley rats for changes in cholesterol level. Rats (n=12) were dosed daily for 12 days with equivalent doses (2.5 mg/kg/day) of either rapamycin or 42-O-(D-fructosylcarbonyl)rapamycin. Cholesterol levels were measured at the 24-hour trough level on day 11. Results (FIG. 9) indicate that rats treated with rapamycin displayed significantly increased levels of cholesterol relative to a vehicle control group, while cholesterol levels in the 42-O-(D-fructosylcarbonyl)rapamycin group were significantly lower (p<0.01) than in the rapamycin group and not significantly different than the vehicle. It is important to note that both compounds showed equivalent efficacy in a heterotopic rat heart transplant model at the same 2.5 mg/kg/day dose used in this study (Example 12). This experiment demonstrates the ability of the rapamycin carbohydrate derivatives to improve the side effect profile of rapamycin while maintaining efficacy.

Example 11

Comparison of Platelet Aggregation due to Rapamycin and 42-O-(D-Fructosylcarbonyl)rapamycin in a Washed Human Platelet Aggregation Assay Platelet aggregation is suspected to be a side effect of rapamycin and has been implicated in increasing chronic rejection and other long term side effects of the use of rapamycin in transplantation. (Ann Babinska et. al., *Enhancement of Human Platelet Aggregation and Secretion Induced by Rapamycin*. (1998) Nephrology Dialysis Transplantation Vol. 13 pp. 3153–3159. These experiments were conducted using fresh washed human platelets stimulated with 2 μM ADP and spiked with either Rapamycin or 42-O-(D-Fructosylcarbonyl)rapamycin at time zero. The treated platelet aggregation was continuously read over a period of 8 to 10 minutes in a ChronoLog™ Platelet Aggregometer.

FIG. 10 shows a plot of percent platelet aggregation versus time for two concentrations of rapamycin, 1 μg/ml and 25 μg/ml. FIG. 10 illustrates that rapamycin induces platelet aggregation in a dose dependent manner. Rapamycin at the 1 μg/ml dose induced platelet aggregation by approximately 20% after 8 minutes. Rapamycin at the 25 μg/ml dose induced platelet aggregation by approximately 70% after 8 minutes. FIG. 11 shows a plot of percent platelet aggregation versus time for washed human platelets, stimulated with 2 μM ADP dosed with 25 μg/ml rapamycin or 25 μg/ml 42-O-(D-Fructosylcarbonyl)rapamycin. FIG. 11 shows that while rapamycin induces nearly 80% platelet aggregation after 8 minutes, 42-O-(D-Fructosylcarbonyl)rapamycin does not exhibit a measurable effect on platelet aggregation in the same time.

Example 12

Graft Survival of Heterotopic Heart Allografts in Rats Receiving Oral 42-O-(D-Fructosylcarbonyl)rapamycin (2.5 and 10 mg/kg/day), Rapamycin (2.5 mg/kg/day), or Vehicle Heterotopic transplants were administered to the abdominal aorta and inferior vena cava of a genetically unmatched (allogenic) heart from Wistar Furth rats to Lewis rats. The controls (vehicle and Rapamycin at 2.5 mg/kg/day) or 42-O-(D-Fructosylcarbonyl)rapamycin, at 2.5 and 10 mg/kg/day were administered once daily by oral gavage to the transplant recipients (6 rats per group) starting 3 days prior to transplantation and continuing for 30 days post-transplantation. If graft dysfunction was noted during the 30-day post-transplantation period, the animal was sacrificed. If the animal survived longer than 30 days post-transplantation, the test and control articles were discontinued and the animal was allowed to continue until graft dysfunction or up to 100 days post-transplantation. The average survival rates for each group of recipient animals are summarized in Table 5 and in FIG. 12. As shown in Table 5, 42-O-(D-Fructosylcarbonyl)rapamycin prolonged survival of the graft at the 2.5 and 10 mg/kg/day dose level by 214 and 341% over the vehicle control. This was similar to the prolonged survival exhibited with rapamycin at the 2.5 mg/kg/day dose. FIG. 12 illustrates that 42-O-(D-Fructosylcarbonyl)rapamycin prolonged survival of the graft over the vehicle as did rapamycin at the 2.5 mg/kg/day dose level. These data demonstrate the immunosuppressive activity of 42-O-(D-Fructosylcarbonyl)rapamycin in preventing graft rejection.

TABLE 5

AVERAGE SURVIVAL RATES AFTER HETEROTOPIC RAT HEART TRANSPLANTS (N = 6)

| | Average Survival Time (days post-transplant) Mean ± SEM | | |
| --- | --- | --- | --- |
| Dose (mg/kg/day) | Vehicle Control | Rapamycin | 42-O-(D-Fructosylcarbonyl)rapamycin |
| 0 | 13 ± 2 | | |
| 2.5 | | 39 ± 4 | 41 ± 4* |
| 10 | | | 57 ± 4 |

*n = 5

Although only some embodiments of the invention are specifically disclosed and described above, it will be appreciated that many modifications and variations of the present invention are possible in light of the above teachings and within the purview of the appended claims without departing from the spirit and intended scope of the invention.

All of the above publications as well as any other references mentioned hereafter are herein incorporated by reference in their entirety to the same extent as if each individual publication was specifically and individually indicated as incorporated herein by reference in its entirety.

What is claimed is:

1. A rapamycin carbohydrate derivative having the structure of formula (I):

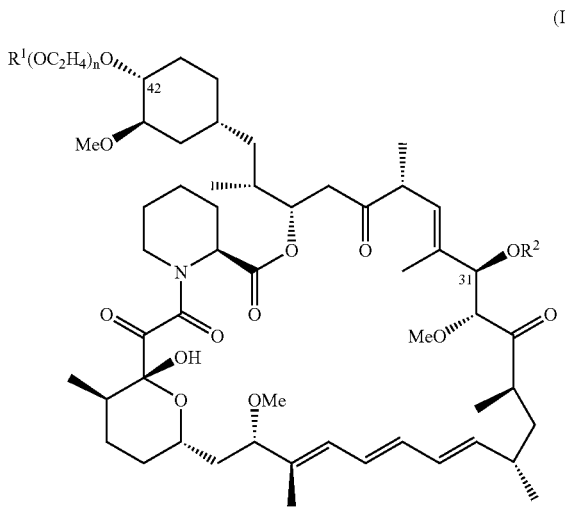

wherein
R¹ and R² are independently hydrogen or X—Z,
wherein n=0 or 1; and
wherein each X is a linker, and each Z is a carbohydrate moiety independently selected from the group consisting of a monosaccharide, oligosaccharide and pseudosugar, wherein Z is attached to X through a hydroxyl oxygen atom of Z with the proviso that R¹ and R² are not both hydrogen and
wherein X is selected from the group consisting of:
(i) —R³C(O)—;
(ii) —C(O)R³—;
(iii) —R³S(O)₂—;
(iv) —S(O)₂R³—;
wherein R³ is selected from the group consisting of:
(a) —(CH₂)$_p$— where p is an interger from 1 to 18;
(b) —(CH₂)$_n$—O—(CH₂)$_m$— where n and m are independently an inter from 2 to 6; and
(c) a bond.

2. The rapamycin carbohydrate derivative of claim 1, wherein R¹ is hydrogen and R² is —X—Z.

3. The rapamycin carbohydrate derivative of claim 2, wherein X is selected from the group consisting of —C(O)— and —SO₂—.

4. The rapamycin carbohydrate derivative of claim 2, wherein X is a single functional group.

5. The rapamycin carbohydrate derivative of claim 2, wherein Z is selected from the group consisting of fructose, fucitol and allose.

6. The rapamycin carbohydrate derivative of claim 5, wherein Z is D-fructose.

7. The rapamycin carbohydrate derivative of claim 2, wherein Z is a monosaccharide derivative wherein at least one of the hydroxyl groups of the monosaccharide is replaced with a hydrogen, an alkoxy, an alkanoate or a halogen group.

8. The rapamycin carbohydrate derivative of claim 1, wherein R¹ is —X—Z and R² is hydrogen.

9. The rapamycin carbohydrate derivative of claim 8, wherein X is selected from the group consisting of —C(O)— and —SO₂—.

10. The rapamycin carbohydrate derivative of claim 8, wherein X is a single functional group.

11. The rapamycin carbohydrate derivative of claim 8, wherein Z is selected from the group consisting of fructose, fucitol and allose.

12. The rapamycin carbohydrate derivative of claim 11, wherein Z is D-fructose.

13. The rapamycin carbohydrate derivative of claim 8, wherein Z is a monosaccharide derivative wherein at least one of the hydroxyl groups of the monosaccharide is replaced with a hydrogen, an alkoxy, an alkanoate or a halogen group.

14. A rampamycin carbohydrate derivative selected from the group consisting of:
42-O-(Methyl-D-glucosylcarbonyl)rapamycin;
42-O-[2-(Methyl-D-glucosylcarbonyloxy)ethyl]rapamycin;
31-O-(Methyl-D-glucosylcarbonyl)rapamycin;
42-O-(2-Hydroxyethyl)-31-O-(methyl-D-glucosylcarbonyl)rapamycin;
42-O-(2-O-Methyl-D-fructosylcarbonyl)rapamycin;
42-O-[2-(2-O-Methyl-D-fructosylcarbonyloxy)ethyl]rapamycin;
42-O-(2-O-Methyl-L-fructosylcarbonyl)rapamycin;
42-O-[2-(2-O-Methyl-L-fructosylcarbonyloxy)ethyl]rapamycin;
31-O-(2-O-Methyl-D-fructosylcarbonyl)rapamycin;
42-O-(2-Hydroxyethyl)-31-O-(2-O-methyl-D-fructosylcarbonyl)rapamycin;
31-O-(2-O-Methyl-L-fructosylcarbonyl)rapamycin;
42-O-(2-Hydroxyethyl)-31-O-(2-O-methyl-L-fructosylcarbonyl)rapamycin;
42-O-(D-Allosylcarbonyl)rapamycin;
42-O-[2-(D-Allosylcarbonyloxy)ethyl]rapamycin;
42-O-(L-Allosylcarbonyl)rapamycin;
42-O-[2-(L-Allosylcarbonyloxy)ethyl]rapamycin;
31-O-(D-Allosylcarbonyl)rapamycin;
42-O-(2-Hydroxyethyl)-31-O-(D-allosylcarbonyl)rapamycin;
31-O-(L-Allosylcarbonyl)rapamycin;
42-O-(2-Hydroxyethyl)-31-O-(L-allosylcarbonyl)rapamycin;
42-O-(D-Fructoslylcarbonyl)rapamycin;
42-O-[2-(D-Fructosylcarbonyloxy)ethyl]rapamycin;
42-O-(L-Fructoslylcarbonyl)rapamycin;
42-O-[2-(L-Fructosylcarbonyloxy)ethyl]rapamycin;
31-O-(D-Fructoslylcarbonyl)rapamycin;
42-O-(2-Hydroxyethyl)-31-O-(D-fructoslylcarbonyl)rapamycin;
31-O-(L-Fructoslylcarbonyl)rapamycin;
42-O-(2-Hydroxyethyl)-31-O-(L-fructoslylcarbonyl)rapamycin;
42-O-(D-Fucitolylcarbonyl)rapamycin;
42-O-[2-(D-Fucitolylcarbonyloxy)ethyl]rapamycin;
42-O-(L-Fucitolylcarbonyl)rapamycin;
42-O-[2-(L-Fucitolylcarbonyloxy)ethyl]rapamycin;
31-O-(D-Fucitolylcarbonyl)rapamycin;
42-O-(2-Hydroxyethyl)-31-O-(D-fucitolylcarbonyl)rapamycin;
31-O-(L-Fucitolylcarbonyl)rapamycin;
42-O-(2-Hydroxyethyl)-31-O-(L-fucitolylcarbonyl)rapamycin;
42-O-(D-Glucalylcarbonyl)rapamycin;
42-O-[2-(D-Glucalylcarbonyloxy)ethyl]rapamycin;
42-O-(D-Glucosylcarbonyl)rapamycin;
42-O-[2-(D-Glucosylcarbonyloxy)ethyl]rapamycin;
42-O-(L-Glucosylcarbonyl)rapamycin;

42-O-[2-(L-Glucosylcarbonyloxy)ethyl]rapamycin;
31-O-(D-Glucalylcarbonyl)rapamycin;
42-O-(2-Hydroxyethyl)-31-O-(D-glucalylcarbonyl)rapamycin;
31-O-(D-Glucosylcarbonyl)rapamycin;
42-O-(2-Hydroxyethyl)-31-O-(D-glucosylcarbonyl)rapamycin;
31-O-(L-Glucosylcarbonyl)rapamycin;
42-O-(2-Hydroxyethyl)-31-O-(L-glucosylcarbonyl)rapamycin;
42-O-(L-Sorbosylcarbonyl)rapamycin;
42-O-(D-Sorbosylcarbonyl)rapamycin;
31-O-(L-Sorbosylcarbonyl)rapamycin;
31-O-(D-Sorbosylcarbonyl)rapamycin;
42-O-[2-(L-Sorbosylcarbonyloxy)ethyl]rapamycin;
42-O-[2-(D-Sorbosylcarbonyloxy)ethyl]rapamycin;
42-O-(2-Hydroxyethyl)-31-O-(D-sorbosylcarbonyl)rapamycin;
42-O-(2-Hydroxyethyl)-31-O-(L-sorbosylcarbonyl)rapamycin;
42-O-(D-Lactalylcarbonyl)rapamycin;
42-O-[2-(D-Lactalylcarbonyloxy)ethyl]rapamycin;
31-O-(D-Lactalylcarbonyl)rapamycin;
42-O-(2-Hydroxyethyl)-31-O-(D-lactalylcarbonyl)rapamycin;
42-O-(D-Sucrosylcarbonyl)rapamycin;.
42-O-[2-(D-Sucrosylcarbonyloxy)ethyl]rapamycin;
31-O-(D-Sucrosylcarbonyl)rapamycin;
42-O-(2-Hydroxyethyl)-31-O-(D-sucrosylcarbonyl)rapamycin;
42-O-(D-Gentobiosylcarbonyl)rapamycin
42-O-[2-(D-Gentobiosylcarbonyloxy)ethyl]rapamycin;
31-O-(D-Gentobiosylcarbonyl)rapamycin
42-O-(2-Hydroxyethyl)-31-O-(D-gentobiosylcarbonyl)rapamycin
42-O-(D-Cellobiosylcarbonyl)rapamycin;
42-O-[2-(D-Cellobiosylcarbonyloxy)ethyl]rapamycin;
31-O-(D-Cellobiosylcarbonyl)rapamycin;
42-O-(2-Hydroxyethyl)-31-O-(D-cellobiosylcarbonyl)rapamycin;
42-O-(D-Turanosylcarbonyl)rapamycin;
42-O-[2-(D-Turanosylcarbonyloxy)ethyl]rapamycin;
31-O-(D-Turanosylcarbonyl)rapamycin;
42-O-(2-Hydroxyethyl)-31-O-(D-turanosylcarbonyl)rapamycin;
42-O-(D-Palatinosylcarbonyl)rapamycin;
42-O-[2-(D-Palatinosylcarbonyloxy)ethyl]rapamycin;
31-O-(D-Palatinosylcarbonyl)rapamycin;
42-O-(2-Hydroxyethyl)-31-O-(D-palatinosylcarbonyl)rapamycin;
42-O-(D-Isomaltosylcarbonyl)rapamycin;
42-O-[2-(D-Isomaltosylcarbonyloxy)ethyl]rapamycin;
31-O-(D-Isomaltosylcarbonyl)rapamycin;
42-O-(2-Hydroxyethyl)-31-O-(D-isomaltosylcarbonyl)rapamycin;
42-O-(D-Maltulosylcarbonyl)rapamycin;
42-O-[2-(D-Maltulosylcarbonyloxy)ethyl]rapamycin;
42-O-(D-Maltosylcarbonyl)rapamycin;
42-O-[2-(D-Maltosylcarbonyloxy)ethyl]rapamycin;
31-O-(D-Maltulosylcarbonyl)rapamycin;
42-O-(2-Hydroxyethyl)-31-O-(D-maltulosylcarbonyl)rapamycin;
31-O-(D-Maltosylcarbonyl)rapamycin;
42-O-(2-Hydroxyethyl)-31-O-(D-maltosylcarbonyl)rapamycin;
42-O-(D-Lactosylcarbonyl)rapamycin;
42-O-[2-(D-Lactosylcarbonyloxy)ethyl]rapamycin;
31-O-(Methyl-D-lactosylcarbonyl)rapamycin;
42-O-(2-Hydroxyethyl)-31-O-(methyl-D-lactosylcarbonyl)rapamycin;
42-O-(D-Melibiosylcarbonyl)rapamycin;
31-O-(D-Melibiosylcarbonyl)rapamycin;
42-O-(2-Hydroxyethyl)-31-O-(D-melibiosylcarbonyl)rapamycin;
42-O-(D-Leucrosylcarbonyl)rapamycin;
42-O-[2-(D-Leucrosylcarbonyloxy)ethyl]rapamycin;
31-O-(D-Leucrosylcarbonyl)rapamycin;
42-O-(2-Hydroxyethyl)-31-O-(D-leucrosylcarbonyl)rapamycin;
42-O-(D-Rafinosylcarbonyl)rapamycin;
42-O-[2-(D-Rafinosylcarbonyloxy)ethyl]rapamycin;
31-O-(D-Rafinosylcarbonyl)rapamycin;
42-O-(2-Hydroxyethyl)-31-O-(D-rafinosylcarbonyl)rapamycin;
42-O-(D-Isomaltotriosylcarbonyl)rapamycin;
42-O-[2-(D-Isomaltosylcarbonyloxy)ethyl]rapamycin;
31-O-(D-Isomaltotriosylcarbonyl)rapamycin;
42-O-(2-Hydroxyethyl)-31-O-(D-isomaltotriosylcarbonyl)rapamycin;
42-O-(D-Cellotetraosylcarbonyl)rapamycin;
42-O-[2-(D-Cellotetraosylcarbonyloxy)ethyl]rapamycin;
31-O-(D-Cellotetraosylcarbonyl)rapamycin;
42-O-(2-Hydroxyethyl)-31-O-(D-cellotetraosylcarbonyl)rapamycin;
42-O-(Valiolylcarbonyl)rapamycin
42-O-[2-(D-Valiolylcarbonyloxy)ethyl]rapamycin;
31-O-(Valiolylcarbonyl)rapamycin
42-O-(2-Hydroxyethyl)-31-O-(valiolylcarbonyl)rapamycin
42-O-(Valiolonylcarbonyl)rapamycin
42-O-[2-(D-Valiolonylcarbonyloxy)ethyl]rapamycin;
31-O-(Valiolonylcarbonyl)rapamycin
42-O-(2-Hydroxyethyl)-31-O-(valiolonylcarbonyl)rapamycin
42-O-(Valienolylcarbonyl)rapamycin
42-O-[2-(D-Valienolylcarbonyloxy)ethyl]rapamycin;
31-O-(Valienolylcarbonyl)rapamycin
42-O-(2-Hydroxyethyl)-31-O-(valienolylcarbonyl)rapamycin
42-O-(Valienoneylcarbonyl)rapamycin
42-O-[2-(D-Valienoneylcarbonyloxy)ethyl]rapamycin;
31-O-(Valienoneylcarbonyl)rapamycin
42-O-(2-Hydroxyethyl)-31-O-(valienoneylcarbonyl)rapamycin.

15. A pharmaceutical composition comprising the rapamycin carbohydrate derivative of claim 1 or a pharmaceutically acceptable salt thereof, and a pharmaceutically acceptable carrier.

16. A method for treating a disease treatable by rapamycin, wherein the disease is selected from the group consisting of transplantation rejection, host vs. graft disease, graft vs. host disease, leukemia, lymphoma, hyperproliferative vascular disorders, autoimmune disease, diseases of inflammation, solid tumors, and fungal infections comprising administering a therapeutically effective amount of a pharmaceutical composition of claim 15 to a subject in need thereof.

17. A medical device wherein said medical device is coated with a rapamycin carbohydrate derivative of claim 1.

18. A medical device of claim 17, wherein the medical device is selected from the group consisting of stents, grafts, and implants.

19. A method for treating a disease, wherein the disease is selected from the group consisting of transplantation rejection, host vs. graft disease, graft vs. host disease, leukemia, lymphoma, hyperproliferative vascular disorders, autoimmune disease, diseases of inflammation, solid tumors, and fungal infections, comprising coadministering a therapeutically effective amount of a pharmaceutical composition of claim 15 to a subject in need thereof with a pharmaceutical composition comprising a compound selected from the group consisting of a cyclosporine or cyclosporine derivative, a steroid, or an immunomodulatory compound.

20. The rapamycin carbohydrate derivative of claim 1 wherein Z is a monosaccharide derivative wherein at least one of the hydroxyl groups of the monosaccharide is replaced with a hydrogen, an alkoxy, an alkanoate or a halogen group.

21. The rapamycin carbohydrate derivative of claim 20, wherein X is selected from the group consisting of —C(O)— and —SO$_2$—.

22. The rapamycin carbohydrate derivative of claim 20, wherein X is a single functional group.

23. A pharmaceutical composition comprising the rapamycin carbohydrate derivative of claim 20 or a pharmaceutically acceptable salt thereof, and a pharmaceutically acceptable carrier.

24. A method for treating a disease wherein the disease is selected from the group consisting of transplantation rejection, host vs. graft disease, graft vs. host disease, leukemia, lymphoma, hyperproliferative vascular disorders, autoimmune disease, diseases of inflammation, solid tumors, and fungal infections comprising administering a therapeutically effective amount of a pharmaceutical composition of claim 20 to a subject in need thereof.

25. A medical device wherein said medical device is coated with a rapamycin carbohydrate derivative of claim 20.

26. The medical device of claim 25, wherein the medical device is selected from the group consisting of stents, grafts, and implants.

27. A method for treating a disease wherein the disease is selected from the group consisting of transplantation rejection, host vs. graft disease, graft vs. host disease, leukemia, lymphoma, hyperproliferative vascular disorders, autoimmune disease, diseases of inflammation, solid tumors, and fungal infections, comprising coadministering a therapeutically effective amount of a pharmaceutical composition of claim 20 to a subject in need thereof with a pharmaceutical composition comprising a compound selected from the group consisting of a cyclosporine or cyclosporine derivative, a steroid, or an immunomodulatory compound.

28. A pharmaceutical composition comprising the rapamycin carbohydrate derivative of claim 2 or a pharmaceutically acceptable salt thereof, and a pharmaceutically acceptable carrier.

29. A method for treating a disease wherein the disease is selected from the group consisting of transplantation rejection, host vs. graft disease, graft vs host disease, leukemia, lymphoma, hyperproliferative vascular disorders, autoimmune disease, diseases of inflammation, solid tumors, and fugal infections comprising administering a therapeutically effective amount of a pharmaceutical composition of claim 28 to a subject in need thereof.

30. A medical device wherein said medical device is coated with a rapamycin carbohydrate derivative of claim 2.

31. A medical device of claim 30, wherein the medical device is selected from the group consisting of stents, grafts, and implants.

32. A method for treating a disease wherein the disease is selected from the group consisting of transplantation rejection, host vs. graft disease, graft vs. host disease, leukemia, lymphoma, hyperproliferative vascular disorders, autoimmune disease, diseases of inflammation, solid tumors, and fungal infections, comprising coadministering a therapeutically effective amount of a pharmaceutical composition of claim 28 to a subject in need thereof with a pharmaceutical composition comprising a compound selected from the group consisting of a cyclosporine or cyclosporine derivative, a steroid, or an immunomodulatory compound.

33. A pharmaceutical composition comprising the rapamycin carbohydrate derivative of claim 8 or a pharmaceutically acceptable salt thereof, and a pharmaceutically acceptable carrier.

34. A method for treating a disease wherein the disease is selected from the group consisting of transplantation rejection, host vs. graft disease, graft vs. host disease, leukemia, lymphoma, hyperproliferative vascular disorders, autoimmune disease, diseases of inflammation, solid tumors, and fungal infections comprising administering a therapeutically effective amount of a pharmaceutical composition of claim 33 to a subject in need thereof.

35. A medical device wherein said medical device is coated with a rapamycin carbohydrate derivative of claim 8.

36. A medical device of claim 35, wherein the medical device is selected from the group consisting of stents, grafts, and implants.

37. A method for treating a disease wherein the disease is selected from the group consisting of transplantation rejection, host vs. graft disease, graft vs. host disease, leukemia, lymphoma, hyperproliferative vascular disorders, autoimmune disease, diseases of inflammation, solid tumors, and fungal infections, comprising coadministering a therapeutically effective amount of a pharmaceutical composition of claim 33 to a subject in need thereof with a pharmaceutical composition comprising a compound selected from the group consisting of a cyclosporine or cyclosporine derivative, a steroid, or an immunomodulatory compound.

38. A pharmaceutical composition comprising the rapamycin carbohydrate derivative of claim 12 or a pharmaceutically acceptable salt thereof, and a pharmaceutically acceptable carrier.

39. A method for treating a disease wherein the disease is selected from the group consisting of transplantation rejection, host vs. graft disease, graft vs. host disease, leukemia, lymphoma, hyperproliferative vascular disorders, autoimmune disease, diseases of inflammation, solid tumors, and fungal infections comprising administering a therapeutically effective amount of a pharmaceutical composition of claim 38 to a subject in need thereof.

40. A medical device wherein said medical device is coated with a rapamycin carbohydrate derivative of claim 38.

41. A medical device of claim 40, wherein the medical device is selected from the group consisting of stents, grafts, and implants.

42. A method for treating a disease wherein the disease is selected from the group consisting of transplantation rejection, host vs. graft disease, graft vs. host disease, leukemia, lymphoma, hyperproliferative vascular disorders, autoimmune disease, diseases of inflammation, solid tumors, and fungal infections, comprising coadministering a therapeutically effective amount of a pharmaceutical composition of claim 38 to a subject in need thereof with a pharmaceutical composition comprising a compound selected from the group consisting of a cyclosporine or cyclosporine derivative, a steroid, or an immunomodulatory compound.

* * * * *